(12) United States Patent
Fallaux et al.

(10) Patent No.: US 8,236,293 B2
(45) Date of Patent: *Aug. 7, 2012

(54) MEANS AND METHODS FOR NUCLEIC ACID DELIVERY VEHICLE DESIGN AND NUCLEIC ACID TRANSFER

(75) Inventors: Frits J. Fallaux, Be Leiderdorp (NL); Robert C. Hoeben, Be Leiden (NL); Abraham Bout, AR Moerkapelle (NL); Domenico Valerio, Leiden (NL); Alex J. van der Eb, TW Oegstgeest (NL); Govert Schoutten, Leiden (NL)

(73) Assignee: Crucell Holland B.V., Leiden (NL)

( * ) Notice: Subject to any disclaimer, the term of this patent is extended or adjusted under 35 U.S.C. 154(b) by 2108 days.

This patent is subject to a terminal disclaimer.

(21) Appl. No.: 11/134,674

(22) Filed: May 19, 2005

(65) Prior Publication Data

US 2005/0221492 A1  Oct. 6, 2005

Related U.S. Application Data

(60) Division of application No. 10/136,139, filed on May 1, 2002, now abandoned, which is a continuation of application No. 09/298,745, filed on Apr. 23, 1999, now Pat. No. 6,395,519, which is a continuation-in-part of application No. 08/793,170, filed as application No. PCT/NL96/00244 on Jun. 14, 1996, now Pat. No. 5,994,128.

(30) Foreign Application Priority Data

Jun. 15, 1995 (EP) .................................. 95201611
Jun. 26, 1995 (EP) .................................. 95201728

(51) Int. Cl.
  *A01N 63/00* (2006.01)
  *C07H 21/02* (2006.01)
  *C12N 5/00* (2006.01)
(52) U.S. Cl. .................... 424/93.2; 536/23.1; 435/325
(58) Field of Classification Search .................. 424/93.2; 536/23.1; 435/325
  See application file for complete search history.

(56) References Cited

U.S. PATENT DOCUMENTS

| | | |
|---|---|---|
| 4,405,712 A | 9/1983 | Vande Woude et al. |
| 4,487,829 A | 12/1984 | Sharp et al. |
| 4,497,796 A | 2/1985 | Salser et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |
| 4,703,008 A | 10/1987 | Lin |
| 4,727,028 A | 2/1988 | Santerre et al. |
| 4,740,463 A | 4/1988 | Weinberg et al. |
| 4,792,525 A | 12/1988 | Ruoslahti et al. |
| 4,797,368 A | 1/1989 | Carter et al. |
| 4,835,260 A | 5/1989 | Shoemaker |
| 4,956,281 A | 9/1990 | Wallner et al. |
| 5,024,939 A | 6/1991 | Gorman |
| 5,047,335 A | 9/1991 | Paulson et al. |
| 5,096,815 A | 3/1992 | Ladner et al. |
| 5,166,320 A | 11/1992 | Wu et al. |
| 5,190,931 A | 3/1993 | Inouye |
| 5,192,539 A | 3/1993 | Van Der Marel et al. |
| 5,198,346 A | 3/1993 | Ladner et al. |
| 5,204,445 A | 4/1993 | Plow et al. |
| 5,208,149 A | 5/1993 | Inouye |
| 5,223,394 A | 6/1993 | Wallner |
| 5,223,409 A | 6/1993 | Ladner et al. |
| 5,240,846 A | 8/1993 | Collins et al. |
| 5,246,921 A | 9/1993 | Reddy et al. |
| 5,332,567 A | 7/1994 | Goldenberg |
| 5,349,053 A | 9/1994 | Landolfi |
| 5,378,618 A | 1/1995 | Sternberg et al. |
| 5,403,484 A | 4/1995 | Ladner et al. |
| 5,436,146 A | 7/1995 | Shenk et al. |
| 5,441,868 A | 8/1995 | Lin |
| 5,443,953 A | 8/1995 | Hansen et al. |
| 5,457,089 A | 10/1995 | Fibi et al. |
| 5,474,935 A | 12/1995 | Chatterjee et al. |

(Continued)

FOREIGN PATENT DOCUMENTS

AU  A-28533/95  3/1996

(Continued)

OTHER PUBLICATIONS

Ghosh-Choudhury et al (The EMBO Journal, 6(6): 1733-1987, 1987).*
Hitt et al (Cell Biology; a laboratory of handbook (J E Cellis Ed) 1: 479-490, 1994).*
Jones et al (Cell, 17: 683-689, 1979).*
Abrahamsen et al., "Construction of an Adenovirus Type 7a E1A Vector," Journal of Virology, Nov. 1997, pp. 8946-8951 vol. 71, No. 11.
Acsadi et al., "Adenovirus-mediated gene transfer into striated muscles," J Mol Med, 1995, pp. 165-180, vol. 73.
Albiges-Rizo et al., "Human Adenovirus Serotype 3 Fiber Protein," Journal of Biological Chemistry, 266(6), 3961-3967 (1991).

(Continued)

Primary Examiner — Gerald Leffers, Jr.
Assistant Examiner — Magdalene Sgagias
(74) Attorney, Agent, or Firm — TraskBritt

(57) ABSTRACT

Cells capable of at least, in part, complementing adenovirus an adenovirus defective in E2A function. Such cells include a nucleic acid-encoding adenovirus E2A or a functional part, derivative, temperature-sensitive mutation and/or analogue thereof, integrated into the cell's genome. Methods for producing an adenovirus particle/vector with a functional deletion of E2A are also disclosed. Such methods involve providing a cell with the functionally deleted adenovirus vector, culturing the cell, and harvesting viral particles. The functional deletion may comprise a deletion in E2A. The nucleic acid-encoding E2A in the cell's genome may lack sequence overlap with the vector, preventing formation of a replication-competent adenovirus or restoration of E2A function. The adenovirus vector may further include a functional deletion in the E1-region. Methods are disclosed for providing cells of an individual with a nucleic acid of interest, without risk of administering simultaneously a replication-competent adenovirus vector, comprising administering the individual an adenovirus vector described herein.

18 Claims, 10 Drawing Sheets

U.S. PATENT DOCUMENTS

| | | |
|---|---|---|
| 5,494,790 A | 2/1996 | Sasaki et al. |
| 5,518,913 A | 5/1996 | Massie et al. |
| 5,521,291 A | 5/1996 | Curiel et al. |
| 5,534,423 A | 7/1996 | Plasson et al. |
| 5,543,328 A | 8/1996 | Mcclelland et al. |
| 5,545,522 A | 8/1996 | Van Gelder et al. |
| 5,547,932 A | 8/1996 | Curiel et al. |
| 5,552,311 A | 9/1996 | Sorscher et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,631,158 A | 5/1997 | Dorai et al. |
| 5,652,224 A | 7/1997 | Wilson et al. |
| 5,670,488 A | 9/1997 | Gregory et al. |
| 5,693,509 A | 12/1997 | Cotten et al. |
| 5,698,443 A | 12/1997 | Henderson et al. |
| 5,707,318 A | 1/1998 | Armentano et al. |
| 5,707,618 A | 1/1998 | Armentano et al. |
| 5,712,136 A | 1/1998 | Wickham et al. |
| 5,731,190 A | 3/1998 | Wickham et al. |
| 5,744,133 A | 4/1998 | Lathe et al. |
| 5,753,500 A | 5/1998 | Shenk et al. |
| 5,756,086 A | 5/1998 | Mcclelland et al. |
| 5,767,078 A | 6/1998 | Johnson et al. |
| 5,770,442 A | 6/1998 | Wickham et al. |
| 5,773,569 A | 6/1998 | Wrighton et al. |
| 5,789,247 A | 8/1998 | Ballay et al. |
| 5,824,544 A | 10/1998 | Armentano et al. |
| 5,830,851 A | 11/1998 | Wrighton et al. |
| 5,835,382 A | 11/1998 | Wilson et al. |
| 5,837,511 A | 11/1998 | Falck-Pedersen et al. |
| 5,846,782 A | 12/1998 | Wickham et al. |
| 5,849,561 A | 12/1998 | Falck-Pedersen |
| 5,851,806 A | 12/1998 | Kovesdi et al. |
| 5,856,152 A * | 1/1999 | Wilson et al. ............... 435/457 |
| 5,856,298 A | 1/1999 | Strickland |
| 5,871,726 A | 2/1999 | Henderson et al. |
| 5,871,727 A | 2/1999 | Curiel |
| 5,871,982 A | 2/1999 | Wilson et al. |
| 5,877,011 A | 3/1999 | Armentano et al. |
| 5,891,690 A | 4/1999 | Massie |
| 5,919,676 A | 7/1999 | Graham et al. |
| 5,922,315 A | 7/1999 | Roy |
| 5,981,275 A | 11/1999 | Armentano et al. |
| 5,994,106 A | 11/1999 | Kovesdi et al. |
| 5,994,128 A | 11/1999 | Fallaux et al. |
| 6,007,806 A | 12/1999 | Lathe et al. |
| 6,033,908 A | 3/2000 | Bout et al. |
| 6,037,453 A | 3/2000 | Jardieu et al. |
| 6,040,174 A | 3/2000 | Imler et al. |
| 6,051,430 A | 4/2000 | Plasterk et al. |
| 6,057,155 A | 5/2000 | Wickham et al. |
| 6,057,299 A | 5/2000 | Henderson |
| 6,077,663 A * | 6/2000 | Curiel et al. ............... 435/6 |
| 6,100,086 A | 8/2000 | Kaplan et al. |
| 6,127,525 A | 10/2000 | Crystal et al. |
| 6,133,028 A * | 10/2000 | Imler et al. ............... 435/325 |
| 6,140,103 A | 10/2000 | Einerhand et al. |
| 6,203,975 B1 | 3/2001 | Wilson |
| 6,204,052 B1 | 3/2001 | Bout et al. |
| 6,210,939 B1 | 4/2001 | Gregory et al. |
| 6,232,105 B1 | 5/2001 | Einerhand et al. |
| 6,238,893 B1 | 5/2001 | Hoeben et al. |
| 6,265,212 B1 | 7/2001 | Fallaux et al. |
| 6,287,857 B1 | 9/2001 | O'riordan et al. |
| 6,306,652 B1 | 10/2001 | Fallaux et al. |
| 6,340,595 B1 | 1/2002 | Vogels et al. |
| 6,358,507 B1 | 3/2002 | Kaplan et al. |
| 6,395,519 B1 | 5/2002 | Fallaux et al. |
| 6,413,776 B1 | 7/2002 | Vogels et al. |
| 6,417,168 B1 | 7/2002 | Greene et al. |
| 6,447,768 B1 | 9/2002 | van Zonneveld et al. |
| 6,475,753 B1 | 11/2002 | Ruben et al. |
| 6,486,133 B1 | 11/2002 | Herlyn et al. |
| 6,492,169 B1 | 12/2002 | Vogels et al. |
| 6,558,948 B1 | 5/2003 | Kochanek et al. |
| 6,602,706 B1 | 8/2003 | Fallaux et al. |
| 6,632,427 B1 | 10/2003 | Finiels et al. |
| 6,653,101 B1 | 11/2003 | Cockett et al. |
| 6,669,942 B2 | 12/2003 | Perricaudet et al. |
| 6,670,188 B1 | 12/2003 | Vogels et al. |
| 6,692,966 B2 | 2/2004 | Fallaux et al. |
| 6,783,980 B2 | 8/2004 | Fallaux et al. |
| 6,844,192 B2 | 1/2005 | Orlando et al. |
| 6,855,544 B1 | 2/2005 | Hateboer et al. |
| 6,869,794 B2 | 3/2005 | Vogels et al. |
| 6,878,549 B1 | 4/2005 | Vogels et al. |
| 6,913,922 B1 | 7/2005 | Bout et al. |
| 6,974,695 B2 | 12/2005 | Vogels et al. |
| 7,029,848 B2 | 4/2006 | Vogels et al. |
| 7,052,881 B2 | 5/2006 | Fallaux et al. |
| 7,105,346 B2 | 9/2006 | Fallaux et al. |
| 7,132,280 B2 | 11/2006 | Bout et al. |
| 7,262,028 B2 | 8/2007 | Van Berkel et al. |
| 7,270,811 B2 | 9/2007 | Bout et al. |
| 7,285,265 B2 | 10/2007 | Vogels et al. |
| 7,291,484 B2 | 11/2007 | Yallop |
| 7,300,657 B2 | 11/2007 | Pau et al. |
| 7,344,883 B2 | 3/2008 | Vogels et al. |
| 7,429,486 B2 | 9/2008 | Van Berkel et al. |
| 7,468,181 B2 | 12/2008 | Vogels et al. |
| 7,470,523 B2 | 12/2008 | Bout et al. |
| 7,491,532 B2 | 2/2009 | Bout et al. |
| 7,504,248 B2 | 3/2009 | Marzio et al. |
| 7,521,220 B2 | 4/2009 | Pau et al. |
| 7,527,961 B2 | 5/2009 | Pau et al. |
| 7,608,431 B2 | 10/2009 | Yallop |
| 7,749,493 B2 | 7/2010 | Havenga et al. |
| 7,820,440 B2 | 10/2010 | Vogels et al. |
| 2002/0006395 A1 | 1/2002 | Perricaudet et al. |
| 2002/0028194 A1 | 3/2002 | Kaplan et al. |
| 2002/0052485 A1 | 5/2002 | Colosi |
| 2002/0102732 A1 | 8/2002 | Fallaux et al. |
| 2002/0116723 A1 | 8/2002 | Grigliatti et al. |
| 2002/0122789 A1 | 9/2002 | Perricaudet et al. |
| 2002/0151032 A1 | 10/2002 | Fallaux et al. |
| 2002/0164802 A1 | 11/2002 | Fallaux et al. |
| 2002/0173039 A1 | 11/2002 | Fallaux et al. |
| 2003/0026783 A1 | 2/2003 | Abina |
| 2003/0044383 A1 | 3/2003 | Henderson et al. |
| 2003/0087437 A1 | 5/2003 | Asada et al. |
| 2003/0092160 A1 | 5/2003 | Bout et al. |
| 2003/0096787 A1 | 5/2003 | Pericaudet et al. |
| 2003/0104626 A1 | 6/2003 | Fallaux et al. |
| 2003/0152553 A1 | 8/2003 | Little et al. |
| 2004/0087027 A1 | 5/2004 | Gregory et al. |
| 2005/0158278 A1 | 7/2005 | Vogels et al. |
| 2005/0196384 A1 | 9/2005 | Vogels et al. |
| 2005/0232900 A1 | 10/2005 | Vogels et al. |
| 2005/0244381 A1 | 11/2005 | Mallet et al. |
| 2005/0260596 A1 | 11/2005 | Fallaux et al. |
| 2005/0265974 A1 | 12/2005 | Pau et al. |
| 2007/0010016 A1 | 1/2007 | McClelland et al. |
| 2007/0041946 A1 | 2/2007 | Bout et al. |
| 2007/0071726 A1 | 3/2007 | Pau et al. |
| 2007/0207461 A1 | 9/2007 | Weggeman et al. |
| 2008/0131461 A1 | 6/2008 | Pau et al. |
| 2008/0171018 A1 | 7/2008 | Bout et al. |
| 2008/0199917 A1 | 8/2008 | Vogels et al. |
| 2008/0206837 A1 | 8/2008 | Vogels et al. |
| 2008/0220014 A1 | 9/2008 | Pau et al. |
| 2009/0017523 A1 | 1/2009 | Weggeman et al. |
| 2009/0023196 A1 | 1/2009 | Fallaux et al. |
| 2009/0253207 A1 | 10/2009 | Vogels et al. |
| 2009/0285879 A1 | 11/2009 | Pau et al. |
| 2010/0015176 A1 | 1/2010 | Vogels et al. |
| 2010/0034774 A1 | 2/2010 | Vogels et al. |
| 2010/0172928 A1 | 7/2010 | Pau et al. |

FOREIGN PATENT DOCUMENTS

| | | |
|---|---|---|
| CA | 2053187 | 4/1993 |
| CA | 2117668 | 9/1995 |
| EP | 0 185 573 | 6/1986 |
| EP | 259212 | 8/1987 |
| EP | 0 411 678 | 2/1991 |
| EP | 95201611.1 | 6/1995 |
| EP | 95201728.3 | 6/1995 |

| | | |
|---|---|---|
| EP | 0 833 934 B1 | 4/1998 |
| EP | 1016726 | 12/1998 |
| EP | 99201545.3 | 5/1999 |
| EP | 1067188 | 7/1999 |
| EP | 1020529 | 11/1999 |
| EP | 0 978 566 A2 | 2/2000 |
| EP | 1 054 064 B1 | 10/2004 |
| EP | 1 550 722 B1 | 6/2007 |
| EP | 1 816 204 A1 | 8/2007 |
| FR | 2 707 664 | 1/1995 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03163 | 2/1993 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/12649 | 6/1994 |
| WO | WO 94/15644 | 7/1994 |
| WO | WO 94/17832 | 8/1994 |
| WO | WO 94/23582 | 10/1994 |
| WO | WO 94/24297 | 10/1994 |
| WO | WO 94/24299 | 10/1994 |
| WO | WO 94/26814 | 11/1994 |
| WO | WO 94/26914 | 11/1994 |
| WO | WO 94/26915 | 11/1994 |
| WO | WO 94/28152 | 12/1994 |
| WO | WO 94/28938 | 12/1994 |
| WO | WO 95/00655 | 1/1995 |
| WO | WO 95/02697 | 1/1995 |
| WO | WO 95/05201 | 2/1995 |
| WO | WO 95/05465 | 2/1995 |
| WO | WO 95/06745 | 3/1995 |
| WO | WO 95/11984 | 5/1995 |
| WO | WO 95/14785 | 6/1995 |
| WO | WO 95/16037 | 6/1995 |
| WO | WO 95/16772 | 6/1995 |
| WO | WO 95/21259 | 8/1995 |
| WO | WO 95/26411 | 10/1995 |
| WO | WO 95/26412 | 10/1995 |
| WO | WO 95/27071 | 10/1995 |
| WO | WO 95/29994 | 11/1995 |
| WO | WO 95/31187 | 11/1995 |
| WO | WO 95/31566 | 11/1995 |
| WO | WO 95/34671 | 12/1995 |
| WO | WO 96/00326 | 1/1996 |
| WO | WO 96/00790 | 1/1996 |
| WO | WO 96/07739 | 3/1996 |
| WO | WO 96/10087 | 4/1996 |
| WO | WO 96/12030 | 4/1996 |
| WO | WO 96/13596 | 5/1996 |
| WO | WO 96/13597 | 5/1996 |
| WO | WO 96/13598 | 5/1996 |
| WO | WO 96/14061 | 5/1996 |
| WO | WO 96/14837 | 5/1996 |
| WO | WO 96/16676 | 6/1996 |
| WO | WO 96/17073 | 6/1996 |
| WO | WO 96/18418 | 6/1996 |
| WO | WO 96/18740 | 6/1996 |
| WO | WO 96/24453 | 8/1996 |
| WO | WO 96/26281 | 8/1996 |
| WO | WO 96/33280 | 10/1996 |
| WO | WO 96/35798 | 11/1996 |
| WO | WO 96/33280 | 12/1996 |
| WO | WO 96/40955 | 12/1996 |
| WO | WO 97/00326 | 1/1997 |
| WO | WO 97/00947 | 1/1997 |
| WO | WO 97/01358 | 1/1997 |
| WO | WO 97/04119 | 2/1997 |
| WO | WO 97/05255 | 2/1997 |
| WO | WO 97/12986 | 4/1997 |
| WO | WO 97/20575 | 6/1997 |
| WO | WO 97/38723 | 10/1997 |
| WO | WO 98/01563 | 1/1998 |
| WO | WO 98/07865 | 2/1998 |
| WO | WO 98/11221 | 3/1998 |
| WO | WO 98/13499 | 4/1998 |
| WO | WO 98/18926 | 5/1998 |
| WO | WO 98/22609 | 5/1998 |
| WO | WO 98/32842 | 7/1998 |
| WO | WO 98/39411 | 9/1998 |
| WO | WO 98/40509 | 9/1998 |
| WO | WO 98/44141 | 10/1998 |
| WO | WO 98/46779 | 10/1998 |
| WO | WO 98/46781 | 10/1998 |
| WO | WO 98/49300 | 11/1998 |
| WO | WO 98/50053 A1 | 11/1998 |
| WO | WO 98/53087 | 11/1998 |
| WO | WO 99/05268 | 2/1999 |
| WO | WO 99/24068 | 5/1999 |
| WO | WO 99/32647 | 7/1999 |
| WO | WO 99/47180 A1 | 9/1999 |
| WO | WO 99/55132 | 11/1999 |
| WO | WO 99/58646 | 11/1999 |
| WO | WO 99/61640 | 12/1999 |
| WO | WO 00/03029 | 1/2000 |
| WO | WO 00/24730 A2 | 5/2000 |
| WO | WO 00/29573 | 5/2000 |
| WO | WO 00/31285 | 6/2000 |
| WO | WO 00/52186 | 9/2000 |
| WO | WO 00/61164 | 10/2000 |
| WO | WO 00/63403 | 10/2000 |
| WO | WO 00/70071 A1 | 11/2000 |
| WO | WO 01/04334 | 1/2001 |
| WO | WO 01/38362 A2 | 5/2001 |
| WO | WO 01/83797 | 11/2001 |
| WO | WO 01/90158 A1 | 11/2001 |
| WO | WO 02/24730 | 3/2002 |
| WO | WO 02/27006 | 4/2002 |
| WO | WO 02/053580 | 7/2002 |
| WO | WO 03/038100 A1 | 5/2003 |
| WO | WO 03/048197 A1 | 6/2003 |
| WO | WO 03/048348 A2 | 6/2003 |
| WO | WO 03/051927 | 6/2003 |
| WO | WO 2004/003176 | 1/2004 |
| WO | WO 2004/099396 | 11/2004 |

OTHER PUBLICATIONS

Alkhatib et al., "Expression of Bicistronic Measles Virus P/C mRNA by Using Hybrid Adenovirus: Levels of C Protein Synthesized in Vivo Are Unaffected by the Presence or Absence of the Upstream P Initiator Codon," Journal of Virology, Nov. 1988, pp. 4059-4068, vol. 62, No. 11.

Alkhatib et al., "High-Level Eurcaryotic in Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.

Amalfitano et al., "Improved adenovirus packaging cell lines to support the growth of replication-defective gene-delivery vectors", Proc. Natl. Acad. Sci. USA, 93:3352-3356, Apr. 1996.

Amalfitano et al., "Isolation and characterization of packaging cell lines that coexpress the adenovirus E1, DNA polymerase, and preterminal proteins: implications for gene therapy," Gene Therapy, 4:258-263, 1997.

Anderson, Nature, "Human gene therapy," Apr. 1998, vol. 392, pp. 25-30.

Armentano et al., "Characterization of an Adenovirus Gene Transfer Vector Containing an E4 Deletion," Human Gene Therapy, 6:1343-1353, Oct. 1995.

Athappilly et al., "The Refined Crystal Structure of Hexon, the Major Coat Protein of Adenovirus Type 2, at 2-9 A Resolution," J. Mol. Biol. (1994) 242, 430-455.

Bai et al., "Mutations That Alter an Arg-Gly-Asp (RGD) Sequence in the Adenovirus Type 2 Penton Base Protein Abolish Its Cell-Rounding Activity and Delay Virus Reproduction in Flat Cells," Journal of Virology, 67(9), 5198-5205 (1993).

Bailey et al., "Phylogenetic Relationships among Adenovirus Serotypes," Virology, 205, 439-452 (1994).

Ball-Goodrich et al., "Parvoviral Target Cell Specificity: Acquisition of Fibrotropism by a Mutant of the Lymphotropic Strain of Minute Virus of Mice Involves Multiple Amino Acid Substitutions within the Capsid," Virology, 184, 175-186 (1991).
Basler et al., "Subgroup B Adenovirus Type 35 Early Region 3 mRNAs Differ from Those of the Subgroup C Adenoviruses," Virology 215, 165-177 (1996).
Basler et al., Sequence of the immunoregulatory early region 3 and flanking sequences of adenovirus type 35, 1996, Gene 170:249-254.
Batra et al., "Receptor-mediated gene delivery employing lectin-binding specificity," Gene Therapy, 1, 255-260 (1994).
Berendsen, Herman J.C., A Glimpse of the Holy Grail, Science, 1998, vol. 282, pp. 642-643.
Berg et al., "High-Level Expression of Secreted Proteins from Cells Adapted to Serum-Free Suspension Culture," BioTechniques, 1993, pp. 972-978, vol. 14, No. 6.
Bernards, Rene, et al., "Characterization of Cells Transformed by Ad5/Ad12 Hybrid Early Region I Plasmids," Virology, 120:422-432, 1982.
Bernards, Rene, et al., "Role of Adenovius Types 5 and 12 Early Region 1b Tumor Antigens in Oncogenic Transformation," Virology, 127:45-53, 1983.
Boursnell et al., "In vitro construction of a recombinant adenovirus Ad2:Ad5," Gene, 13, 311-317 (1981).
Bout et al., "Improved helper cells for RCA-free production of E1-deleted recombinant adenovirus vectors," Cancer Gene Therapy, 1996, pp. S24, vol. 3, No. 6.
Bout et al., "Production of RCA-free batches of E1-deleted recombinant adenoviral vectors on PER.C6," Nucleic Acids Symp. Ser. 1998, XP-002115716, pp. 35-36.
Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.
Bridge et al., "Adenovirus Early Region 4 and Viral DNA Synthesis," Virology 193, 794-801 (1993).
Brody et al., "Adenovirus-Mediated In Vivo Gene Transfer," Annals New York Academy of Sciences pp. 90-100, 1994.
Brough et al., "Construction, Characterization, and Utilization of Cell Lines Which Inducibly Express the Adenovirus DNA-Binding Protein," Virology, 190:624-634, 1992.
Brough et al., "Restricted changes in the adenovirus DNA-binding protein that lead to extended host range or temperature sensitive phenotypes," Journal of Virology, vol. 55, pp. 206-212, 1985.
Brough et al., "Multiple Functions of the Adenovirus DNA-Binding Protein Are Required for Efficient Viral DNA Synthesis," Virology, 196:269-281, 1993.
Brough et al., "Stable Cell Lines for Complementation of Adenovirus Early Regions E1, E2A and E4," Abstract Book CSH Conference on Gene Therapy, 42, 1996.
Brough et al., "A Gene Transfer Vector-Cell Line System for Complete Functional Complementation of Adenovirus Early Regions E1 and E4," Journal of Virology, 70(9):6497-6501, Sep. 1996.
Brown et al., "Evaluation of Cell Line 293 for Virus isolation in Routine Viral Diagnosis," Journal of Clinical Microbiology, Apr. 1986, pp. 704-708, vol. 23, No. 4.
Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.
Byrd et al., Malignant transformation of human embryo retinoblasts by cloned adenovirus 12 DNA, Nature, Jul. 1, 1982, pp. 69-71, vol. 298.
Caillet-Boudin et al., "Functional and Structural Effects of an Ala to Val Mutation in the Adenovirus Serotype 2 Fibre," J. Mol. Biol., 217, 477-486 (1991).
Caravokyri et al., Constitutive Episomal Expression of Polypeptide IX (pIX) in a 293-Based Cell Line Complements the Deficiency of pIX Mutant Adenovirus Type 5, Journal of Virology, Nov. 1995, pp. 6627-6633, vol. 69, No. 11.
Carroll et al., Abstract, Differential Infection of Receptor-modified Host Cells by Receptor-Specific Influenza Viruses, Virus Research, Sep. 1985, pp. 165-179, vol. 3, No. 2.

Cell line: 293, Cell type: human embryonal kidney, copyright 2004 DSMZ GmbH, <http://www.dsmz.de/human_and_animal_cell_lines/info.php?dsmz_nr_305&term=293&highlight>.
Certificate of deposit of the PER.C6 cell line (ECACC deposit under No. 96022940), 1996.
Chiu et al., Folding & Design, "Optimizing energy potentials for success in protein tertiary structure prediction," May 1998, pp. 223-228, vol. 3.
Chroboczek et al., "The Sequence of the Genome of Adenovirus Type 5 and Its Comparison with the Genome of Adenovirus Type 2," Virology, 1992, pp. 280-285, vol. 186.
Chroboczek et al., Adenovirus Fiber, Current Topics in Microbiology and Immunology 1995;199 (Pt 1) pp. 163-200.
Chu et al., "Cell targeting with retroviral vector particles containing antibodyBenvelope fusion proteins," Gene Therapy, 1, 292-299 (1994).
Ciccarone et al., "Lipofectamine 2000 Reagent for Transfection of Eukaryotic Cells," Focus, 1999, pp. 54-55, vol. 21, No. 2.
Colby et al., "Adenovirus Type 5 Virions Can Be Assembled in Vivo in the Absence of Detectable Polypeptide IX," Journal of Virology, Sep. 1981, pp. 997-980, vol. 39, No. 3.
Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.
Cotton et al., "High-efficiency receptor-mediated delivery of small and large (48 kilobase gene constructs using the endosome-disruption activity of defective or chemically inactivated adenovirus particles," Proc. Natl. Acad. Sci. USA, 89, 6094-6098 (1992).
Cotton et al., "Transferrin-polycation-mediated introduction of DNA into human leukemic cells: Stimulation by agents that affect the survival of transfected DNA or modulate transferring receptor levels," Proc. Natl. Acad. Sci. USA, 87, 4033-4037 (1990).
Crawford-Miksza et al., "Adenovirus Serotype Evolution Is Driven by Illegitimate Recombination in the Hypervariable Regions of the Hexon Protein," Virology, 224, 357-367 (1996).
Crawford-Miksza et al., "Analysis of 15 Adenovirus Hexon Proteins Reveals the Location and Structure of Seven Hypervariable Regions Containing Serotype-Specific Residues," Journal of Virology, Mar. 1996, p. 1836-1844.
Crawford-Miksza et al., Strain Variation in Adenovirus Serotypes 4 and 7a Causing Acute Respiratory Disease, Journal of Clinical Microbiology, Apr. 1999, pp. 1107-1112, vol. 37, No. 4.
Crompton et al., "Expression of a foreign epitope on the surface of the adenovirus hexon," J. Gen. Virol., 75(1), 133-139 (1994).
Cronan, Abstract, Biotination of Proteins in-vivo a post-translational modification to label purify and study proteins, Journal of Biological Chemistry, Jun. 25, 1990, pp. 10327-10333, vol. 265, No. 18.
Crystal, Ronald G., "Transfer of Genes to Humans: Early Lessons and Obstacles to Success," Science, 270, 404-410 (1995).
Curiel et al., "Adenovirus enhancement of transferring-polylysine-mediated gene delivery," Proc. Natl. Acad. Sci. USA, 88, 8850-8854 (1991).
Curiel et al., "High-Efficiency Gene Transfer Mediated by Adenovirus Coupled to DNABPolylysine Complexes," Human Gene Therapy, 3, 147-154 (1992).
De Jong et al., "Adenovirus Isolates From Urine of Patients with Acquired Immunodeficiency Syndrome," The Lancet, Jun. 11, 1983 pp. 1293-1296.
De Jong et al., Adenoviruses from Human Immunodeficiency Virus-Infected Individuals, Including Two Strains That Represent New Candidate Serotypes Ad50 and Ad51 of Species B1 and D, Respectively, Journal of Clinical Microbiology, Dec. 1999, p. 3940-45, vol. 37, No. 12, American Society for Microbiology.
Declaration of Amine Kamen, including six exhibits: (1) Conference schedule of sixth conference on Protein Expression in Animal Cells (6th PEACe) held in Mont-Tremblant, Canada, Sep. 7-11, 2003; (2) Abstract of Presentation of Dr. van der Eb entitled Isolation of adenovirus E1-transformed human cell lines; PER.C6™ as a platform for production of proteins; (3) Shaw et al., Preferential transformation of human neuronal cells by human adenoviruses and the origin of HEK 293 cells, FASEB Journal, pp. 869-887, vol. 16 (listed below separately); (4) Byrd et al., Malignant transformation of human embryo retinoblasts by cloned adenovirus 12 DNA, Nature, Jul. 1, 1982, pp. 69-71, vol. 298 (listed below separately); (5) Schiedner et al., Efficient Transformation of Primary Human Amniocytes by E1 Functions of Ad5: Generation of New Cell Lines for Adenoviral Vector Production, Human Gene Ther., 2000, pp. 2105-2116, vol. 11 (listed below separately).

Defer et al., "Human Adenovirus-Host Cell Interactions: Comparative Study with Members of Subgroups B and C," Journal of Virology, 64(8), 3661-3673 (1990).

Deonarain, "Ligand-targeted receptor-mediated vectors for gene delivery," (1998) Expert Opin. Ther. Pat. 8: 53-69.

Dijkema et al., "Transformation of Primary Rat Kidney Cells by DNA Fragments of Weakly Oncogenic Adenoviruses," Journal of Virology, Dec. 1979, p. 943-950.

Douglas et al., Abstract, "Strategies to accomplish targeted gene delivery to muscle cells employing tropism-modified adenoviral vectors" Neuromuscular Disorders, Pergamon Press, GB, vol. 7, Jul. 1997, pp. 284-298, XP002079944 ISSN: 0960-8966.

DuBridge et al., "Analysis of Mutation in Human Cells by Using an Epstein-Barr Virus Shuttle System," Molecular and Cellular Biology, Jan. 1987, pp. 397-387, vol. 7, No. 1.

Dupuit et al., "Regenerating Cells in Human Airway Surface Epithelium Represent Preferential Targets for Recombinant Adenovirus," Human Gene Therapy, 6, 1185-1193 (1995).

Eck et al., "Gene-Based Therapy," (1996) Goodman & Gillman's The Pharmacological Basis of Therapeutics, Mc-Graw-Hill, New York, N.Y., pp. 77-101.

Endo et al., Growth of Influenza A Virus in Primary, Differentiated Epithelial Cells Derived from Adenoids, Journal of Virology, Mar. 1996, pp. 2055-2058, vol. 70, No. 3.

Engelhardt et al., "Ablation of E2A in recombinant adenoviruses improves transgene persistence and decreases inflammatory response in mouse liver," Proceeding of the National Sciences of USA, vol. 91, pp. 6196-6200, 1994.

Etienne-Julan et al., "The efficiency of cell targeting by recombinant retroviruses depends on the nature of the receptor and the composition of the artificial cellBvirus linker," Journal of General Virology, 73, 3251-3255 (1992).

European Search Report 05 10 0732, Apr. 7, 2005.

Falgout et al., "Characterization of Adenovirus Particles Made by Deletion Mutants Lacking the Fiber Gene," Journal of Virology, 62(2), 622-625 (1988).

Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917. Abstract.

Fallaux et al., "Characterization of 911: A New Helper Cell Line for the Titration and Propagation of Early Region 1-Deleted Adenoviral Vectors," Human Gene Therapy, 7:215-222, 1996.

Fields et al., "Fields Virology," Second Edition, pp. 28-30, 87.

George et al "Gene therapy progress and prospects: adenoviral vectors," Gene Therapy (2003) 10, 1135-1141.

Ghosh-Choudhury et al., Protein IX, a minor component of the human adenovirus capsid, is essential for the packaging of the full length genomes, The EMBO Journal, 1987, pp. 1733-1739, vol. 6, No. 6.

Gibco cell culture, A guide to Serum-Free Cell Culture, www.invitrogen.com.

Gorecki, "Prospects and problems of gene therapy: an update," (2001) Expert Opin. Emerging Drugs 6(2): 187-98.

Gorziglia et al., "Elimination of both E1 and E2a from Adenovirus Vectors Further Improves Prospects for In Vivo Human Gene Therapy," Journal of Virology, 70(6):4173-4178, Jun. 1996.

Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached to the Gal(beta-1-4)GlcNAc(beta-1-2)Man(alpha-1-3) branch of diantennary oligosaccharides from secreted recombinant beta-trace protein, Eur. J. Biochem, 1995, pp. 718-725, vol. 232, No. 3, Berlin, Germany.

Graham et al., "Size and location of the transforming region in human adenovirus type 5 DNA," Nature, Oct. 25, 1974, pp. 687-691, vol. 251.

Graham et al., Characteristics of a Human Cell Line Transformed by DNA from Human Adenovirus Type 5, J. Gen. Virol., 1977, pp. 59-72, vol. 36, Great Britain.

Grand et al., "Modulation of the level of expression of cellular genes in adenovirus 12-infected and transformed human cells," Eur Mol Biol Organ J. 1986, 5 (6) 1253-1260. Abstract.

Grand et al., "The high levels of p53 present in adenovirus early region 1-transformed human cells do not cause up-regulation of MDM2 expression," Virology, 1995, vol. 210, No. 2, pp. 323-334. Abstract.

Greber et al., "Stepwise Dismantling of Adenovirus 2 during Entry into Cells," Cell, 75, 477-486 (1993).

Green et al "Evidence for a repeating cross-sheet structure in the adenovirus fibre," EMBO Journal, 2(8), 1357-1365 (1983).

Grodzicker, Terri, et al., "Expression of Unselected Adenovirus Genes in Human Cells Cotransformed with the HSV-1 tk Gene and Adenovirus 2 DNA," Cell, 21:453-463, Sep. 1980.

Grubb et al., Abstract, Inefficient gene transfer by adenovirus vector to cystic fibrosis airway epithelia of mice and humans, Nature, 371, 802-806 (1994).

Gurunathan et al., American Association of Immunologists, "CD40 Ligand/Trimer DNA Enhances Both Humoral and Cellular Immune Responses and Indicates Protective Immunity to Infectious and Tumor Challenge," 1998, 161:4563-4571.

Han et al., "Ligand-directed retroviral targeting of human breast cancer cells," Proc. Natl. Acad. Sci. USA, 92, 9747-9751 (1995).

Hardy et al., "Construction of Adenovirus Vectors through CRE-lox Recombination," Journal of Virology, 71(3):1842-1849, Mar. 1997.

He et al., "A simplified system for generating recombinant adenoviruses," Proc. Natl. Acad. Sci. USA vol. 95, pp. 2509-2514, Mar. 1998.

Hehir et al., "Molecular Characterization of Replication-Competent Variants of Adenovirus Vectors and Genome Modifications to Prevent Their Occurrence," Journal of Virology, 70(12):8459-8467, Dec. 1996.

Henry et al., "Characterization of the Knob Domain of the Adenovirus Type 5 Fiber Protein Expressed in *Escherichia coli*," Journal of Virology, 68(8), 5239-5246 (1994).

Hidaka, Chisa, et al., "CAR-dependent and CAR-independent pathways of adenovirus vector-mediated gene transfer and expression in human fibroblasts," 103(4) The Journal of Clinical Investigation 579-87 (Feb. 1999).

Hierholzer et al., "Adenoviruses from Patients with AIDS: A Plethora of Serotypes and a Description of Five New Serotypes of Subgenus D (Types 43-47)," The Journal of Infectious Diseases vol. 158, No. 4 Oct. 1988.

Hitt et al., "Construction and Propagation of Human Adenovirus Vectors," Cell Biology, 1994, pp. 479-490, vol. 1, Academic Press, San Diego, California.

Hollister et al., Stable expression of mammalian beta1,4-galactosyltransferase extends the N-glycosylation pathway in insect cells, Glycobiology, 1998, pp. 473-480, vol. 8, No. 5, IRL Press, United Kingdom.

Holterman et al., Novel Replication-Incompetent Vector Derived from Adenovirus Type 11 (Ad11) for Vaccination and Gene Therapy: Low Seroprevalence and Non-Cross-Reactivity with Ad5, Journal of Virology, Dec. 2004, pp. 13207-13215, vol. 78, No. 23.

Hong et al., "The Amino Terminus of the Adenovirus Fiber Protein Encodes the Nuclear Localization Signal," Virology, 185(2), 758-767 (1991).

Horvath et al., "Nonpennissivity of Human Peripheral Blood Lymphocytes to Adenovirus Type 2 Infection," Journal of Virology, 62(1), 341-345 (1988).

Huang et al., "Upregulation of Integrins $\alpha v\beta 3$ and $\alpha v\beta 5$ on Human Monocytes and T Lymphocytes Facilitates Adenovirus-Mediated Gene Delivery," Journal of Virology, 69(4), 2257-2263 (1995).

Imler et al., "Novel complementation cell lines derived from human lung carcinoma A549 cells support the growth of E1-deleted adenovirus vectors," Gene Therapy, vol. 3: p. 75-84, 1996.

Jenkins et al., Getting the glycosylation right: Implications for the biotechnology industry, Nature Biotechnology, Aug. 1996, pp. 975-981, vol. 14, No. 8, Nature Publishing, US.

Jolly; "Viral vector systems for gene therapy," 1994, Cancer Gene Therapy, vol. 1, No. 1: 51-64.

Kang et al., "Molecular Cloning and Physical Mapping of the DNA of Human Adenovirus Type 35," Acta Microbiologica Hungarica 36 (1), pp. 67-75 (1989).

Kang et al., "Relationship of E1 and E3 Regions of Human Adenovirus 35 to Those of Human Adenovirus Subgroups A, C and D," Acta Microbiologica Hungarica 36 (4), pp. 445-457 (1989).

Karayan et al., "Oligomerization of Recombinant Penton Base of Adenovirus Type 2 and Its Assembly with Fiber in Baculovirus-Infected Cells," Virology, 202, 782-795 (1994).

Kass-Eisler et al., "Quantitative determination of adenovirus-mediated gene delivery to rat cardiac myocytes in vitro and in vivo," Proc. Natl. Acad. Sci. USA, 90, 11498-11502 (1993).

Kmiec, "Gene Therapy," American Scientist, vol. 87, pp. 240, 1999.

Komoriya et al., The Minimal Essential Sequence for a Major Cell Type-specific Adhesion Site (CS1) within the Alternatively Spliced Type III Connecting Segment Domain of Fibronectin Is Leucine-Aspartic Acid-Valine, Journal of Biological Chemistry, 266(23), 15075-15079 (1991).

Krasnykh et al., "Generation of Recombinant Adenovirus Vectors With Modified Fibers for Altering Viral Tropism" Journal of Virology, The American Society for Microbiology, US, vol. 70, No. 10, Oct. 1, 1996, pp. 6839-6846, XP002067518 ISSN: 0022-538X.

Krougliak et al., Development of Cell Linds Capable of Complementing E1, E4 and Protein IX Defective Adenovirus Type 5 Mutants, Human Gene Therapy, Dec. 1995, pp. 1575-1586, vol. 6.

Lattanzi, Laura, et al., "High Efficiency Myogenic Conversion of Human Fibroblasts by Adenoviral Vector-mediated MyoD Gene Transfer," 101(10) J. Clin. Invest. 2119-28 (May 1998).

Lee et al., "The constitutive expression of the immunomodulatory gp 19k protein in E1-, E3- adenoviral vectors strongly reduces the host cytotoxic T cell response against the vector," Gene Therapy (1995) 2, 256-262.

LeMarchand et al., "Adenovirus-mediated transfer of a recombinant human 1-antitrypsin cDNA to human endothelial cells," Proc. Natl. Acad. Sci. USA, vol. 89, pp. 6482-6486, Jul. 1992.

Lemckert et al., Generation of a novel replication-incompetent adenoviral vector derived from human adenovirus type 49: manufacture on PER.C6 cells, tropism and immunogenicity, Journal of General Virology, 2006, pp. 2891-2899, vol. 87.

Levrero et al., "Defective and nondefective adenovirus vectors for expressing foreign genes in vitro and in vivo," Gene, 101 (1991) 195-202.

Li et al., "Genetic Relationship between Thirteen Genome Types of Adenovirus 11, 34, and 35 with Different Tropisms," Intervirology 1991;32:338-350.

Lieber et al., "Recombinant Adenoviruses with Large Deletions Generated by CRE-Mediated Excision Exhibit Different Biological Properties Compared with First-Generation Vectors In Vitro and In Vivo," Journal of Virology, 70:8944-8960, Dec. 1996.

Liu et al., Molecular Basis of the inflammatory response to adenovirus vectors. Gene Therapy, 2003 10, 935-40.

Lochmuller, H., et al., "Emergence of Early Region 1-Containing Replication-Competent Adenovirus in Stocks of Replication-Defective Adenovirus Recombinants (E1+E3) During Multiple Passages in 293 Cells", Human Gene Therapy, 5:1485-1491, Dec. 1994.

Lopez et al., Efficient production of biologically active human recombinant proteins in human lymphoblastoid cells form integrative and episomal expression vectors, Gene, 1994, pp. 285-291, vol. 148.

Louis, Nathalie, et al., "Cloning and Sequencing of the Cellular-Viral Junctions from the Human Adenovirus Type 5 Transformed 293 Cell Line", Virology, 233:423-429, 1997.

Lutz et al., "The Product of the Adenovirus Intermediate Gene IX Is a Transcriptional Activator," Journal of Virology, Jul. 1997, pp. 5102-5109, vol. 71, No. 7.

Manservigi et al., "Protection from Herpes Simplex Virus Type 1 Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.

Maraveyas et al., Targeted Immunotherapy B an update with special emphasis on ovarian cancer, Acta Oncologica, 32(7/8), 741-746 (1993).

Marck, Christian, "'DNA Strider': a 'C' program for the fast analysis of DNA and protein sequences on the Apple Macintosh family of computers," Nucleic Acids Research, 1988, pp. 1829-1836, vol. 16, No. 5.

Marketing Authorization and Scientific Discussion for Xigris.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Mastrangeli et al., "Sero-Switch" Adenovirus-Mediated in Vivo Gene Transfer: Circumvention of Anti-Adenovirus Humoral Immune Defenses Against Repeat Adenovirus Vector Administration by Changing the Adenovirus Serotype, Human Gene Therapy, 7, 79-87 (1996).

Mathias et al., "Multiple Adenovirus Serotypes Use αv Integrins for Infection," Journal of Virology, 68(10), 6811-6814 (1994).

Matsui et al., Adenovirus 2 Peptide IX Gene Is Expressed Only on Replicated DNA Molecules, Molecular and Cellular Biology, Dec. 1986, pp. 4149-4154, vol. 6, No. 12.

Mautner et al., "Recombination in Adenovirus: Analysis of Crossover Sites in Intertypic Overlap Recombinants," Virology, 139, 43-52, (1984).

Merriam-Webster Dictionary (on line) retrieved from the internet<URL:htpp://www. m-w.com/cgi-bin/dictionary, "derive," 2002.

Merten et al., Production of Influenza Virus in Cell Cultures for Vaccine Preparation, Exp Med Biol., 1996, pp. 141-151, vol. 397.

Michael et al., "Addition of a short peptide ligand to the adenovirus fiber protein," Gene Therapy, 2, 660-668 (1995).

Michael et al., "Binding-incompetent Adenovirus Facilitates Molecular Conjugate-mediated Gene Transfer by the Receptor-mediated Endocytosis Pathway," Journal of Biological Chemistry, 268(10), 6866-6869 (1993).

Miller et al., "Targeted vectors for gene therapy," FASEB Journal, 9, 190-199 (1995).

Minch et al., Tissue Plasminogen Activator Coexpressed in Chinese Hamster Ovary Cells with alpha(2,6)-Sialyltransferase Contains NeuAc-alpha(2,6)Gal-beta(1,4)Glc-N-AcR Linkages, Biotechnol. Prog., 1995, pp. 348-351, vol. 11, No. 3.

Mitani et al., "Rescue, propagation, and partial purification of a helper virus-dependent adenovirus vector," Proc. Natl. Acad. Sci., Apr. 1995, pp. 3854-3858, vol. 92.

Nan et al., Development of an Ad7 cosmid system and generation of an Ad7DE1DE3HIVMN env/rev recombinant virus, Gene Therapy, 2003, pp. 326-336, vol. 10.

NCBI database excerpt: Locus AC_000008 (human adenovirus type 5).

NCBI Entrez Nucleotide accession No. NC_002018.

NCBI Entrez Nucleotide accession No. U38242.

NCBI Entrez Nucleotide accession No. X02996 J01967 J01968 J01970 J01971 J01972 J01974 J01976 J01977 J01978 J01979 K00515 V00025 V00026 V00027 V00029.

Neda et al., "Chemical Modification of an Ecotropic Murine Leukemia Virus Results in Redirection of Its Target Cell Specificity," Journal of Biological Chemistry, 266(22), 14143-14146 (1991).

Nemerow et al., "Adenovirus entry into host cells: a role for αv integrins," Trends In Cell Biology, 4, 52-55 (1994).

Nemerow et al., "The Role of αv Integrins in Adenovirus Infection," Biology of Vitronectins and their Receptors, 177-184 (1993).

Neumann et al., "Generation of influenza A viruses entirely from cloned cDNAs," Proc. Natl. Acad. Sci., Aug. 1999, pp. 9345-9350, vol. 96.

Ngo et al., The Protein Folding Problem and Tertiary Structure Prediction, "Computational Complexity, Protein Structure Prediction, and the Levinthal Paradox," 1994, Merz et al. (editors), Birkhauser, Boston, MA, pp. 433 and 492-495.

Notice of Opposition to a European Patent by Serono International S.A. filed against Patent No. 0 833 934 (Jul. 5, 2005).

Novelli et al., "Deletion Analysis of Functional Domains in Baculovirus-Expressed Adenovirus Type 2 Fiber," Virology, 185, 365-376 (1991).

Opposition against European patent 1 108 878 B1 filed Oct. 5, 2005 in the name and on behalf of CEVEC Pharmaceuticals GmbH.

Opposition against European patent 1 161 548 B1 filed Nov. 16,2005, in the name and on behalf of CEVEC Pharmaceuticals GmbH.

Opposition against European patent 1108787 filed Oct. 5, 2005 in the name and on behalf of Probiogen AG.

Opposition lodged by Cevec Pharmaceuticals GmbH against European Patent 0 833 934 (Jul. 5, 2005).

Orkin et al., "Reports and Recommendations of the Panel to Assess the NIH Investment in Research on Gene Therapy", 21 pages, Dec. 7, 1995.

Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Parker et al., Effect of Neutralizing Sera on Factor X-Mediated Adenovirus Serotype 5 Gene Transfer, Journal of Virology, Jan. 2009, pp. 479-783, vol. 83, No. 1.

Parkinson et al., "Stable Expression of a Secretable Deletion Mutant of Recombinant Human Thrombomodulin in Mammalian Cells, The Journal of Biological Chemistry," Jul. 25, 1990, pp. 12602-12610, vol. 265, No. 21.

Pau et al., Abstract, The human cell line PER.C6 provides a new manufacturing system for the production of influenza vaccines, Vaccine, Mar. 21, 2001, pp. 2716-2721, vol. 19, No. 17-19.

Paul et al., Increased Viral Titer Through Concentration of Viral Harvests from Retroviral Packaging Lines, Human Gene Therapy, 1993, pp. 609-615, vol. 4.

Pazur et al., Abstract, Oligosaccharides as immunodeterminants of erythropoietin for two sets of anti-carbohydrate antibodies, Journal of Protein Chemistry, Nov. 2000, pp. 631-635, vol. 19, No. 8.

PCT International Search Report, PCT/NL00/00247, dated Oct. 9, 2000, 3 pages.

PCT International Search Report, PCT/NL00/00325 dated Sep. 7, 2000.

PER.C6TM Cell Line (Crucell), printout of the third slide of the www.niaid.hib.gov/hivvaccines/pdf/Ledwith.pdf <http://www.niaid.hih.gov/hivvaccines/pdf/Ledwith.pdf>.

Peshwa et al., "Cultivation of Mammalian Cells as Aggregates in Bioreactors: Effect of Calcium Concentration on Spatial Distribution of Viability," 1993, pp. 179-187, vol. 41.

Peteranderl et al., "Trimerization of the Heat Shock Transcription Factor by a Triple-Stranded—Helical Coiled-Coil," Biochemistry, 31, 12272-12276 (1992).

Pleschka et al., "A Plasmid-Based Reverse Genetics System for Influenza A Virus," Journal of Virology, Jun. 1996, pp. 4188-4192, vol. 70, No. 6.

Prelich et al., Functional Characterization of Thermolabile DNA-Binding Proteins That Affect Adenovirus DNA Replication, Journal of Virology, Mar. 1986, pp. 883-892, vol. 57, No. 3.

Prince, "Gene Transfer: A Review of Methods and Applications," Pathology (1998), 30, pp. 335-347.

Pring-Åkerblom et al., "Sequence Characterization and Comparison of Human Adenovirus Subgenus B and E Hexons," Virology, 212, 232-36 (1995).

PubMed listing of abstracts (visited Apr. 10, 2005) <http://www.ncbi.nlm.nih.gov/entrez/query.fcgi?CMD=search&DB=pubmed.

Ragot et al., Abstract, "Efficient adenovirus-mediated transfer of a human minidystrophin gene to skeletal muscle of mdx mice" Nature, Macmillan Journals Ltd. London, GB, vol. 361, No. 6413, 1993, pp. 647-650, XP002162515 ISSN: 0028-0836.

Rao et al., "The adenovirus E1A proteins induce apoptosis, which is inhibited by the E1B 19-kDa and Bcl-2 proteins," Proc. Natl. Acad. Sci., Aug. 1992, pp. 7742-746, vol. 89.

Rea et al., "Highly efficient transduction of human monocyte-derived dendritic cells with subgroup B fiber-modified adenovirus vectors enhances transgene-encoded antigen presentation to cytotoxic T cells." Journal of Immunology, (Apr. 15, 2000) 166 (8) 5236-44., XP002192775.

Reddy et al., Development of adenovirus serotype 35 as a gene transfer vector, Virology, 2003, pp. 384-393, vol. 311.

Reina et al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Rice et al., Multiple Effects on the 72-kDa, Adenovirus-Specified DNA Binding Protein on the Efficiency of Cellular Transformation, Virology, 1987, pp. 366-376, vol. 156.

Robbins et al., "Viral Vectors for Gene Therapy," Pharmacol. Ther. vol. 80, No. 1, pp. 35-47, 1998.

Roberts et al., "Three-Dimensional Structure of the Adenovirus Major Coat Protein Hexon," Science, 232, 1148-51 (1986).

Roberts, Bryan E., et al., "Individual Adenovirus Type 5 Early Region 1A Gene Products Elicit Distinct Alterations of Cellular Morphology and Gene Expression," Journal of Virology, pp. 404-413, Nov. 1985.

Roelvink et al., The Coxsackievirus-Adenovirus Receptor Protein Can Function as a Cellular Attachment Protein for Adenovirus Serotypes from Subgroups A, C, D, E, and F, Journal of Virology, Oct. 1998, p. 7909-7915, vol. 72, No. 10.

Romano, "Gene Transfer in Experimental Medicine," Drug & News Perspectives, vol. 16, No. 5, 2003, 13 pages.

Rosenfeld et al., "In Vivo Transfer of the Human Cystic Fibrosis Transmembrane Conductance Regulator Gene to the Airway Epithelium," Cell, vol. 68, pp. 143-155, Jan. 10, 1992.

Rowe et al., "Establishment and Characterization of Hamster Cell Lines Transformed by Restriction Endonuclease Fragments of Adenovirus 5," Journal of Virology, Jan. 1984, pp. 162-170, vol. 49, No. 1.

Roy et al; Circumvention of Immunity to the Adenovirus major Coat Protein Hexon; Journal of Virology, Aug. 1998, pp. 6875-6879, vol. 72, No. 8.

Ruley, H. Earl, "Adenovirus early region 1A enables viral and cellular transforming genes to transform primary cells in culture," Nature, Aug. 1983, pp. 602-606, vol. 304.

Russell et al., "Retroviral vectors displaying functional antibody fragments," Nucleic Acids Research, 21(5), 1081-1085 (1993).

Russell, "Replicating Vectors for Gene Therapy of Cancer: Risks, Limitations and Prospects," European Journal of Cancer, 1994, vol. 30A, No. 8, pp. 1165-1171.

Sabatie et al., "Process Development for the Production of Second Generation Adenovirus Vectors for Gene Transfer in Clinical Protocols," Abstract Book 14th Meeting on Animal Cell Technology, BI-3, 1996.

Sabourin et al., "The molecular regulation of myogenesis," (2000) Clin. Genet. 57(1): 16-25.

Sambrook et al., "Molecular Cloning—A Laboratory Manual," 3rd edition, 2001, Cold Spring Harbor Laboratory Press, Cold Spring Harbor, New York.

Schaack et al., "Adenovirus Type 5 Precursor Terminal Protein-Expressing 293 and HeLa Cell Lines," Journal of Virology, 69(7):4079-4085, Jul. 1995.

Schiedner et al., Efficient Transformation of Primary Human Amniocytes by E1 Functions of Ad5: Generation of New Cell Lines for Adenoviral Vector Production, Human Gene Ther., 2000, pp. 2105-2116, vol. 11.

Schmitz et al., Worldwide Epidemiology of Human Adenovirus Infections, American Journal of Epidemiology, 1982, pp. 455-466, vol. 117, No. 4.

Schnurr et al., "Two New Candidate Adenovirus Serotypes," Intervirology 1993;36:79-83.

Schulick et al., "Established Immunity Precludes Adenovirus-mediated Gene Transfer in Rat Carotid Arteries," The Journal of Clinical Investigation vol. 99, No. 2, Jan. 1997, 209-219.

Segerman et al.: "Adenovirus types 11p and 35p show high binding efficiencies for committed hematopoietic cell lines and are infective to these cell lines" Journal of Virology, The American Society for Microbiology, US, vol. 74, No. 3, Feb. 2000, pp. 1457-1467, XP002161682 ISSN: 0022538X.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.

Shaw et al., Preferential transformation of human neuronal cells by human adenoviruses and the origin of HEK 293 cells, FASEB Journal, pp. 869-887, vol. 16, 2002.

Shayakhmetov et al., "Efficient Gene Transfer into Human CD34+ Cells by a Retargeted Adenovirus Vector," Journal of Virology, Mar. 2000, p. 2567-2583.

Signäs et al., "Adenovirus 3 Fiber Polypeptide Gene: Implications for the Structure of the Fiber Protein," Journal of Virology, 53(2), 672-678 (1985).

Silver et al., "Interaction of Human Adenovirus Serotype 2 with Human Lymphoid Cells," Virology, 165, 377-387 (1988).

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.

Stevenson et al., "Selective Targeting of Human Cells by a Chimeric Adenovirus Vector Containing a Modified Fiber Protein," 1997, Journal of Virology, vol. 71: 4782-4790.

Stewart et al., "Difference imaging of adenovirus: bridging the resolution gap between X-ray crystallography and electron microscopy," EMBO Journal, 12(7), 2589-2599 (1993).

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

Stratford-Perricaudet LD et al.: "Widespread Long-Term Gene Transfer to Mouse Skeletal Muscles and Heart" Journal of Clinical Investigation, New York, NY, US, vol. 90 No. 2, Aug. 1992, ISSN: 0021-9738.

Stratford-Perricaudet, Leslie, et al., "Gene Transfer Into Animals: The Promise of Adenovirus, Human Gene Transfer," 219:51-61, 1991.

Submissions of Opponent Cevec to the European opposition proceedings, received at the EPO on Sep. 22, 2006.

Submissions of Opponent Serono International to the European opposition proceedings, received at the EPO on Sep. 22, 2006.

Submissions of Patentee to the European opposition proceedings, received at the EPO on Sep. 25, 2006, including one cited document: Zavizion et al., Transformation of Human Corneal Endothelial Cells by Microinjection of Oncogenes, 1990, Bull Exp Biol Med, pp. 519-522, vol. 109, Plenum Publishing corporation (listed separately below).

Submissions of Patentee to the European opposition proceedings, transmitted to the EPO on Oct. 12, 2006 including three cited documents listed separately below.

Thomas et al., Progress and Problems with the Use of Viral Vectors for Gene Therapy, Nature Publishing Group, May 2003, pp. 346-358, vol. 4.

Toogood et al., "The Adenovirus Type 40 Hexon: Sequence, Predicated Structure and Relationship to Other Adenovirus Hexons," J. gen. Virol (1989), 70, 3203-3214.

Trapnell et al., "Gene therapy using adenoviral vectors," Current Opinion in Biotechnology, 5:617-625, 1994.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1999 (visited Sep. 30, 2005) <http://www.fda.gov.cber.minutes/0910evolv.txt>.

Ulfendahl et al., A novel adenovirus-2 E1A mRNA encoding a protein with transcription activation properties, The EMBO Journal, 1987, pp. 2037-2044, vol. 6, No. 7, IRL Press Limited, Oxford, England.

Vaessen, R.T.M.J., "Adenovirus E1A-Mediated Regulation of Class I MHC Expression," The EMBO Journal, 5(2):335-341, 1986.

Vaessen, R.T.M.J., "Different Adenovirus E1A-Controlled Properties of Transformed Cells Require Different Levels of E1A Expression," Gene, pp. 247-254, 1987.

Valderrama-Leon et al., "Restriction Endonuclease Mapping of Adenovirus 35, a Type Isolated from Immunocompromised Hosts," Journal of Virology, Nov. 1985, p. 647-650.

Vanhaesbroeck, Bart et al., "Modulation of Cellular Susceptibility to the Cytotoxic/Cytostatic Action of Tumor Necrosis Factor by Adenovirus E1 Gene Expression Is Cell Type-Dependent," Virology, 176:362-368, 1990.

Verma et al., Nature, "Gene therapy-promises, problems and prospects," Sep. 1997, vol. 389, pp. 239-242.

Vogels et al., Replication-Deficient Human Adenovirus Type 35 Vectors for Gene Transfer and Vaccination: efficient Human Cell Infection and ByPass of Preexisting Adenovirus Immunity, J. Virology, 2003, pp. 8263-8271, vol. 77, No. 15.

Vos et al., "Characterization of Adenovirus Type 5 Insertion and Deletion Mutants Encoding Altered DNA Binding Proteins," Virology, 172, pp. 634-642, 1989.

Wadell, "Molecular Epidemiology of Human Adenoviruses," Microbiology and Immunology, vol. 110 pp. 191-220, 1984.

Wagner et al., "Coupling of adenovirus to transferring-polylysine/DNA complexes greatly enhances receptor-mediated gene delivery and expression of transfected genes," Proc. Natl. Acad. Sci. USA, 89, 6099-6103 (1992).

Wang et al., "A packaging cell line for propagation of recombinant adenovirus vectors containing two lethal gene-region deletions," Gene Therapy, 2:775-783, 1995.

Watson et al., "An Antigenic Analysis of the Adenovirus Type 2 Fibre Polypeptide," Journal of Virology, 69, 525-535 (1988).

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Weinberg et al., "A cell line that supports the growth of a defective early region 4 deletion mutant of human adenovirus type 2," Proc. Natl. Sci. USA, vol. 80, pp. 5383-5386, Sep. 1983.

White et al., "Adenovirus E1B 19-Kilodalton Protein Overcomes the Cytotoxicity of E1A Proteins," Journal of Virology, Jun. 1991, pp. 2968-2978, vol. 65, No. 6.

White et al., "Role of Adenovirus E1B Proteins in Transformation: Altered Organization of Intermediate Filaments in Transformed Cells That Express the 19-Kilodalton Protein," Molecular and Cellular Biology, Jan. 1990, pp. 120-130, vol. 10, No. 1.

White et al., "Specific disruption of intermediate filaments and the nuclear lamina by the 19-kDa product of the adenovirus E1B oncogene," Proc. Natl. Acad. Sci., Dec. 1989, pp. 9886-9890, vol. 86.

White et al., "The 19-Kilodalton Adenovirus E1B Transforming Protein Inhibits Programmed Cell Death and Prevents Cytolysis by Tumor Necrosis Factor alpha," Molecular and Cellular Biology, Jun. 1992, pp. 2570-2580, vol. 12, No. 6.

Wickham et al., "Increased In Vitro and In Vivo Gene Transfer by Adenovirus Vectors Containing Chimeric Fiber Proteins," Journal of Virology, Nov. 1997, p. 8221-8229.

Wickham et al., "Integrin αvβ5 Selectively Promotes Adenovirus Mediated Cell Membrane Permeabilization," Journal of Cell Biology, 127(1), 257-264 (1994).

Wickham,e t al.; Integrins αvβ3 and αvβ5 Promote Adenovirus Internalization but Not Virus Attachment; Cell, vol. 73, 309-319, Apr. 23, 1993.

Woodworth et al., "Transformation of Differentiated Rat Hepatocytes with Adenovirus and Adenovirus DNA," Journal of Virology, Nov. 1987, pp. 3570-3579, vol. 61, No. 11.

Xu et al., Approaches to improving the kinetics of adenovirus-delivered genes and gene products, Advanced Drug Delivery Reviews, 2005, pp. 781-802, vol. 57.

Yallop et al., "PER.C6® Cells for the Manufacture of Biopharmaceutical Proteins," Modern Biopharmaceuticals, Ed. J. Knablein, 2005, Wiley-VCH Verlag GmbH & Co. KGaA, Weinheim, Germany.

Yan et al., Novel Asn-linked oligosaccharides terminating in GalNAcbeta(1-4)[Fucalpha(1-3)]GlcNAcbeta(1-.) are present in recombinant human Protein C expressed in human kidney 293 cells, Glycobiology, 1993, pp. 597-608, vol. 3. No. 6.

Yang et al., "Cellular immunity to viral antigens limits E1-deleted adenoviruses for gene therapy," Proc. Natl. Acad. Sci. USA, vol. 91, pp. 4407-4411, May 1994.

Yeager et al., Constructing immortalized human cell lines, Current Opinion Biotechnology, 1999, pp. 465-469, vol. 10.

Yeh et al., Adenoviral Vectors, pp. 25-42 of "Concepts in Gene Therapy," Publisher: Walter de Gruyter, New York.

Yeh et al., "Efficient Dual Transcomplementation of Adenovirus E1 and E4 Regions from a 293-Derived Cell Line Expressing a Minimal E4 Functional Unit," Journal of Virology, 70(1):559-565, Jan. 1996.

Yu et al., "Enhanced c-erbB-2/neu expression in human ovarian cancer cells correlates with more severe malignancy that can be suppressed by E1A," Cancer Res., 1993, 53 (4) 891-8. Abstract.

Zavizion et al., Transformation of Human Corneal Endothelial Cells by Microinjection of Oncogenes, 1990, Bull Exp Biol Med, pp. 519-522, vol. 109, Plenum Publishing corporation.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

Zhong et al.: Abstract, "Recombinant Advenovirus Is an Efficient and Non-Pertubing Genetic Vector for Human Dendritic Cells" European Journal of Immunology, Weinheim, DE, vol. 29, No. 3, 1999, pp. 964-972, XP000938797 ISSN: 0014-2980.

Zhou et al., "Development of a Complementing Cell Line and a System for Construction of Adenovirus Vectors with E1 and E2a Deleted," Journal of Virology, 70(1):7030-7038, Oct. 1996.

European Opponent's Statement on Grounds of Appeal dated Sep. 14, 2007.

Figure 2 by Opponent 01 (D52).

Van Den Elsen, et al., The relationship between region E1a and E1b of human adenoviruses in cell transformation, Gene, 1982, pp. 175-185, vol. 18 (D53).

Kawarabayasi et al., Structure of viral DNA in a rat cell line transformed by the cloned EcoRi-C fragment of adenovirus 12, Nucleic Acids Research, 1985, pp. 6591-6604, vol. 13, No. 18 (D54).

Kimura et al., Nucleotide sequence of the transforming early region E1b of adenovirus type 12 DNA: structure and gene organization, and comparison with those of adenovirus type 5 DNA, 9(23):6571-89 (1981), (D55).

Vanhaesebroeck et al., "Modulation of Cellular Susceptibility to the Cytotoxic/Cytostatic Action of Tumor Necrosis Factor by Adenovirus E1 Gene Expression is Cell Type-Dependent", Virology, 176(2), pp. 362-368, Jun. 1990.

Wang et al., "A packaging cell line for propagation of recombinant adenovirus vectors containing two lethal gene-region deletions", Gene Therapy, 2:775-783, 1995.

Yeh et al., "Efficient Dual Transcomplementation of Adenovirus E1 and E4 Regions from a 293-Derived Cell Line Expressing a Minimal E4 Functional Unit", Journal of Virology, 70(1):559-565, Jan. 1996.

Zhou et al., "Development of a Complementing Cell Line and a System for Construction of Adenovirus Vectors with E1 and E2a Deleted", Journal of Virology, 70(1):7030-7038, Oct. 1996.

U.S. Appl. No. 09/444,284, filed Nov. 19, 1999, Gene Delivery Vectors Provided With a Tissue Tropism for Smooth Muscle Cells, and/or Endothelial Cells.

U.S. Appl. No. 09/573,740, filed May 18, 2000, Serotype of Adenovirus and Uses Thereof.

U.S. Appl. No. 09/621,593, filed Jul. 21, 2000, Means and Methods for Raising Antibody Concentration in Compartments of the Body of a Non-Human Animal.

U.S. Appl. No. 09/665,472, filed Sep. 20, 2000, Gene Delivery Vectors Provided With a Tissue Tropism for Dendritic Cells.

U.S. Appl. No. 09/843,894, filed Apr. 27, 2001, AAV Vector Production.

U.S. Appl. No. 09/900,062, filed Jul. 6, 2001, Packaging Systems for Human Recombinant Adenovirus to Be Used in Gene Therapy.

U.S. Appl. No. 09/901,836, filed Jul. 10, 2001, Methods and Means for Targeted Gene Delivery.

U.S. Appl. No. 09/953,280, filed Sep. 14, 2001, Chimaeric Adenoviruses.

U.S. Appl. No. 10/010,645, filed Nov. 13, 2001, Gene Delivery Vectors With Cell Type Specificity for Mesenchymal Stem Cells.

U.S. Appl. No. 10/038,271, filed Oct. 23, 2001, Packaging Systems for Human Recombinant Adenovirus to be used in Gene Therapy.

U.S. Appl. No. 10/125,751, filed Apr. 18, 2002, Packaging Systems for Human Recombinant Adenovirus to Be Used in Gene Therapy.

U.S. Appl. No. 10/136,139, filed May 1, 2002, Means and Methods for Nucleic Acid Delivery Vehicle Design and Nucleic Acid Transfer.

U.S. Appl. No. 10/164,076, filed Jun. 4, 2002, Methods and Compositions for Genetically Modifying Primate Bone Marrow Cells.

U.S. Appl. No. 10/196,688, filed Jul. 15, 2002, Adeno-Associated Virus and Adenovirus Chimeric Recombinant Viruses Useful for the Integration of Foreign Genetic Information Into Chromosomal DNA of Target Cells.

U.S. Appl. No. 10/219,414, filed Aug. 15, 2002, Stocks of Replication Deficient Adenovirus.

U.S. Appl. No. 10/231,735, filed Aug. 28, 2002, Interleukin-3 Gene Therapy for Cancer.

U.S. Appl. No. 10/234,007, filed Sep. 3, 2002, Recombinant Protein Production in a Human Cell.

U.S. Appl. No. 10/305,435, filed Nov. 25, 2002, Methods and Means for Enhancing Skin Transplantation Using Gene Delivery Vehicles Having Tropism for Primary Fibroblasts, as Well as Other Uses Thereof (Primaire Fibroblasten).

U.S. Appl. No. 10/381,088, filed Mar. 20, 2003, Adenoviral Vectors Provided With a Tropism for Dendritic Cells.

U.S. Appl. No. 10/381,857, filed Aug. 13, 2003, Adenoviral Vectors for Gene Delivery in Skeletal Muscle Cells or Myoblasts.

U.S. Appl. No. 10/396,548, filed Mar. 25, 2003, Packaging Systems for Human Recombinant Adenovirus to be Used in Gene Therapy.

U.S. Appl. No. 10/432,105, filed May 20, 2003, Adenoviral Replicons.

U.S. Appl. No. 10/494,140, filed Apr. 29, 2004, Methods and Means for Producing Proteins With Predetermined Post-Translational Modifications.

U.S. Appl. No. 10/499,298, filed Oct. 25, 2004, Efficient Production of F(AB')2 Fragments in Mammalian Cells.

U.S. Appl. No. 10/512,589, filed Oct. 25, 2004, Means and Methods for the Production of Adenovirus Vectors.

U.S. Appl. No. 10/618,526, filed Jul. 11, 2003, Packaging Systems for Human Recombinant Adenovirus to be Used in Gene Therapy.

U.S. Appl. No. 10/644,256, filed Aug. 20, 2003, Efficient Production of IgA in Recombinant Mammalian Cells.

U.S. Appl. No. 10/783,510, filed Feb. 20, 2004, Means and Methods for Fibroblast-Like or Macrophage-Like Cell Transduction.

U.S. Appl. No. 10/790,562, filed Mar. 1, 2004, Recombinant Protein Production in a Human Cell.

U.S. Appl. No. 10/808,681, filed Mar. 25, 2004, Melanoma Associated Peptide Analogues and Vaccines Against Melanoma.

U.S. Appl. No. 10/850,140, filed May 20, 2004, Packaging Systems for Human Recombinant Adenovirus to Be Used in Gene Therapy.

U.S. Appl. No. 10/951,102, filed Sep. 27, 2004, Serotypes of Adenovirus and Uses Thereof.

U.S. Appl. No. 11/018,669, filed Dec. 20, 2004, Gene Delivery Vectors Provided With a Tissue Tropism for Smooth Muscle Cells, and/or Endothelial Cells.

U.S. Appl. No. 11/039,767, filed Jan. 18, 2005, Recombinant Production of Mixtures of Antibodies.

U.S. Appl. No. 11/070,890, filed Mar. 2, 2005, Recombinant Protein Production in Permanent Amniocytic Cells That Comprise Nucleic Acid Encoding Adenovirus E1A and E1B Proteins.

Amalfitano et al., "Isolation and characterization of packaging cell lines that coexpress the adenovirus E1, Dna polymerase, and preterminal proteins: implications for gene therapy", Gene Therapy, 4:258-263, 1997.

Armentano et al., "Characterization of an Adenovirus Gene Transfer Vector Containing an E4 Deletion", Human Gene Therapy, 6:1343-1353, Oct. 1995.

Brough et al., "A Gene Transfer Vector-Cell Line System for Complete Functional Complementation of Adenovirus Early Regions E1 and E4", Journal of Virology, 70(9):6497-6501, Sep. 1996.

Brough et al., "Construction, Characterization, and Utilization of Cell Lines Which Inducibly Express the Adenovirus DNA-Binding Protein", Virology, 190:624-634, 1992.

Brough et al., Stable Cell Lines for Complementation of Adenovirus Early Regions E1, E2A and E4; Abstract Book CSH Conference on Gene Therapy, 42, 1996.

Caravokyri et al., "Constitutive Episomal Expression of Polypeptide IX (pIX) in a 293-Based Cell Line Complements the Deficiency of pIX Mutant Adenovirus Type 5", Journal of Virology, 69(11):6627-6633, Nov. 1995.

Chroboczek et al., "The Sequence of the Genome of the Adenovirus Type 5 and Its Comparison with the Genome of Adenovirus Type 2," Virology, 186:280-285, 1992.

Fallaux et al., "Characterization of 911: A New Helper Cell Line for the Titration and Propagation of Early Region 1-Deleted Adenoviral Vectors", Human Gene Therapy, 7:215-222, 1996.

Fisher et al., "Recombinant Adenovirus Deleted of All Viral Genes for Gene Therapy of Cystic Fibrosis", Virology, 217:11-22, 1996.

Gao et al., "Biology of Adenovirus Vectors with E1 and E4 Deletions for Liver-Directed Gene Therapy", Journal of Virology, 70(12):8934-8943, Dec. 1996.

Gorziglia et al., "Elimination of both E1 and E2a from Adenovirus Vectors Further Improves Prospects for In Vivo Human Gene Therapy", Journal of Virology, 70(6):4173-4178, Jun. 1996.

Hardy et al., "Construction of Adenovirus Vectors through Cre-lox Recombination", Journal of Virology, 71(3):1842-1849, Mar. 1997.

Hehir et al., "Molecular Characterization of Replication-Competent Variants of Adenovirus Vectors and Genome Modifications to Prevent Their Occurrence", Journal of Virology, 70(12):8459-8467, Dec. 1996.

Imler et al., "Novel complementation cell lines derived from human lung carcinoma A549 cells support the growth of E1-deleted adenovirus vectors", Gene Therapy, 3:75-84, 1996.

Kornberg, Arthur, "DNA Replication", W.H. Freeman and Company, San Francisco, 8 pages.

Krougliak et al., "Development of Cell Lines Capable of Complementing E1, E4, and Protein IX Defective Adenovirus Type 5 Mutants", Human Gene Therapy, 6:1575-1586, Dec. 1995.

Lieber et al., "Recombinant Adenoviruses with Large Deletions Generated by Cre-Mediated Excision Exhibit Different Biological Properties Compared with First-Generation Vectors In Vitro and In Vivo", Journal of Virology, 70:8944-8960, Dec. 1996.

Ngo et al., "in the Protein Folding Problem and Tertiary Structure Prediction", Merz et al., (ed.), Birkhauser, Boston, MA, pp. 433 and 492-495, 1994.

Sabatie et al., "Process Development for the Production of Second Generation Adenovirus Vectors for Gene Transfer in Clinical Protocols", Abstract Book 14th Meeting on Animal Cell Technology, BI-3, 1996.

Schaack et al., "Adenovirus Type 5 Precursor Terminal Protein-Expressing 293 and HeLa Cell Lines", Journal of Virology, 69(7):4079-4085, Jul. 1995.

Acsadi et al., Adenovirus-mediated gene transfer into striated muscles, J Mol Med, 1995, pp. 165-180, vol. 73.

Berg et al., High-Level Expression of Secreted Proteins from Cells Adapted to Serum-Free Suspension Culture, BioTechniques, 1993, pp. 972-978, vol. 14, No. 6.

Colby et al., Adenovirus Type 5 Virions Can Be Assembled In Vivo in the Absence of Detectable Polypeptide IX, Journal of Virology, Sep. 1981, pp. 997-980, vol. 39, No. 3.

Gallimore et al., Transformation of Human Embryo Retinoblasts with Simian Virus 40, Adenovirus and ras Oncogenes, Anticancer Research, 1986, pp. 499-508, vol. 6.

GenBank Accession No. X02996.1, 1993, "Adenovirus type 5 left 32% of the genome."

Graham et al., Size and location of the transforming region in human adenovirus type 5 DNA, Nature, Oct. 25, 1974, pp. 687-691, vol. 251.

Hitt et al., Construction and Propagation of Human Adenovirus Vectors, Cell Biology, 1994, pp. 479-490, vol. 1, Academic Press, San Diego, California.

Marck, Christian, 'DNA Strider': a 'C' program for the fast analysis of DNA and protein sequences on the Apple Macintosh family of computers, Nucleic Acids Research, 1988, pp. 1829-1836, vol. 16, No. 5.

Mitani et al., Rescue, propagation, and partial purification of a helper virus-dependent adenovirus vector, Proc. Natl. Acad. Sci., Apr. 1995, pp. 3854-3858, vol. 92.

NCBI database excerpt: Locus AC_000008 (human adenovirus type 5), 1992.

Peshwa et al., Cultivation of Mammalian Cells as Aggregates in Bioreactors: Effect of Calcium Concentration on Spatial Distribution of Viability, 1993, pp. 179-187, vol. 41.

Rao et al., The adenovirus E1A proteins induce apoptosis, which is inhibited by the E1B I9-kDa and Bcl-2 proteins, Proc. Natl. Acad. Sci., Aug. 1992, pp. 7742-7746, vol. 89.

Rhim, Johng S., Development of Human Cell Lines from Multiple Organs, 2000, Annals New York Academy of Sciences, pp. 16-25.

Rowe et al., Establishment and Characterization of Hamster Cell Lines Transformed by Restriction Endonuclease Fragments of Adenovirus 5, Journal of Virology, Jan. 1984, pp. 162-170, vol. 49, No. 1.

Ruley, H. Earl, Adenovirus early region 1A enables viral and cellular transforming genes to transform primary cells in culture, Nature, Aug. 1983, pp. 602-606, vol. 304.

Sambrook et al., Molecular Cloning—A Laboratory Manual, 3rd edition, 2001, Cold Spring Harbor Laboratory Press, Cold Spring Harbor, New York.

White et al., Adenovirus E1 B 19-Kilodalton Protein Overcomes the Cytotoxicity of E1A Proteins, Journal of Virology, Jun. 1991, pp. 2968-2978, vol. 65, No. 6.

White et al., Role of Adenovirus E1B Proteins in Transformation: Altered Organization of Intermediate Filaments in Transformed Cells That Express the 19-Kilodalton Protein, Molecular and Cellular Biology, Jan. 1990, pp. 120-130, vol. 10, No. 1.

White et al., Specific disruption of intermediate filaments and the nuclear lamina by the 19-kDa product of the adenovirus E1B oncogene, Proc. Natl. Acad. Sci., Dec. 1989, pp. 9886-9890, vol. 86.

White et al., The 19-Kilodalton Adenovirus E1B Transforming Protein Inhibits Programmed Cell Death and Prevents Cytolysis by Tumor Necrosis Factor alpha, Molecular and Cellular Biology, Jun. 1992, pp. 2570-2580, vol. 12, No. 6.

Woodworth et al., Transformation of Differentiated Rat Hepatocytes with Adenovirus and Adenovirus DNA, Journal of Virology, Nov. 1987, pp. 3570-3579, vol. 61, No. 11.

U.S. Appl. No. 11/593,280, filed Nov. 6, 2006, Van Berkel et al., Recombinant Production of Mixtures of Antibodies.

U.S. Appl. No. 12/221,021, filed Jul. 29, 2008, Van Berkel et al. Recombinant Production of Mixtures of Antibodies.

U.S. Appl. No. 11/348,661, filed Feb. 7, 2006, Valerio et al., Methods and Means for Targeted Gene Delivery.

U.S. Appl. No. 12/291,881, filed Nov. 14, 2008, Hateboer et al., Recombinant Protein Production in a Human Cell.

U.S. Appl. No. 11/586,316, filed Oct. 25, 2006, Bout et al., Serotypes of Adenovirus and Uses Thereof.

U.S. Appl. No. 11/980,222, filed Oct. 29, 2007, Bout et al., Serotypes of Adenovirus and Uses Thereof.

U.S. Appl. No. 11/207,626, filed Aug. 18, 2005, Havenga et al., Chimaeric Adenoviruses.

U.S. Appl. No. 12/455,086, filed May 28, 2009, Vogels et al., Gene Delivery Vectors Provided With a Tissue Tropism for Smooth Muscle Cells, and/or Endothelial Cells.

U.S. Appl. No. 11/657,202, filed Jan. 24, 2007, Opstelten et al., Methods and Means for Producing Proteins With Predetermined Post-Translational Modifications.

U.S. Appl. No. 11/888,776, filed Aug. 1, 2007, Opstelten et al., Methods and Means for Producing Proteins With Predetermined Post-Translational Modifications.

U.S. Appl. No. 11/800,871, filed May 7, 2007, Vogels et al., Means and Methods for the Production of Adenovirus Vectors.

* cited by examiner

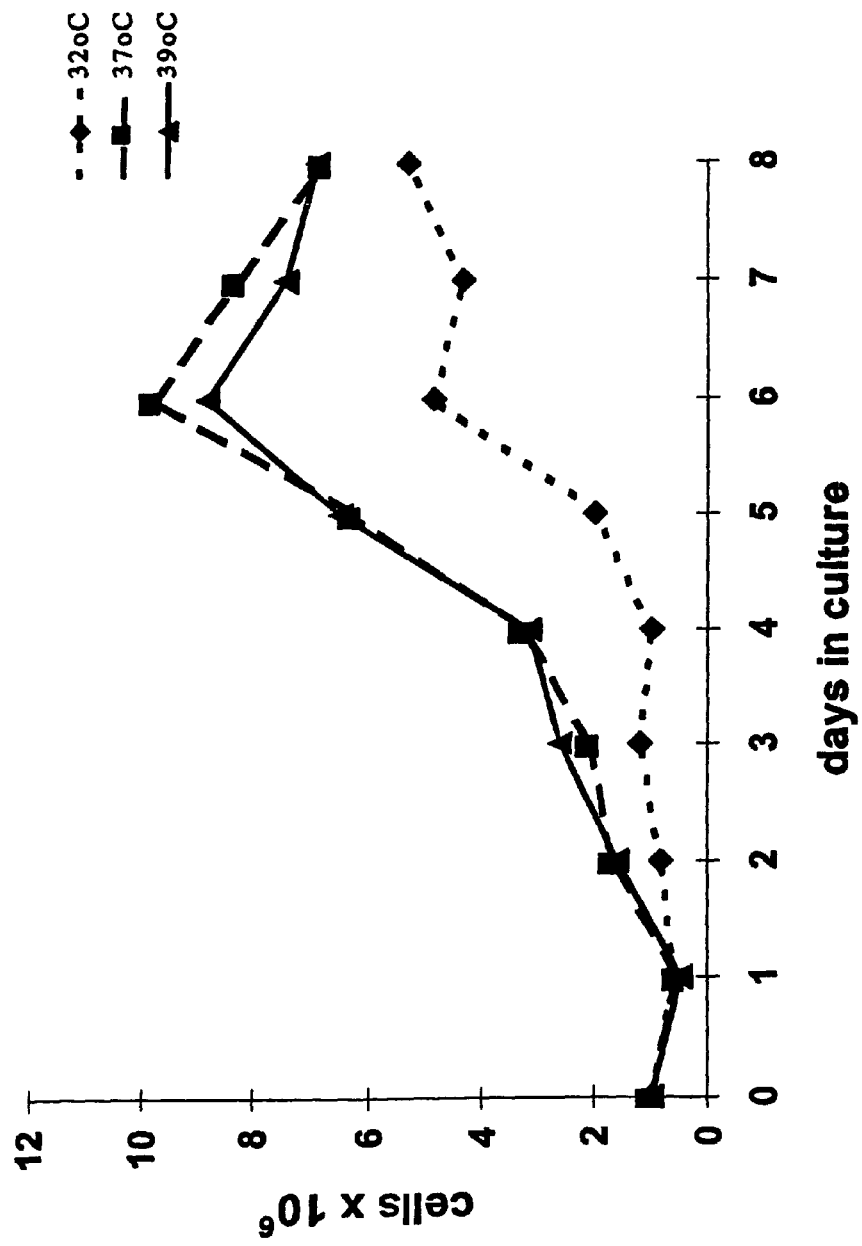
Figure 1  Temperature dependent growth of PER.C6

Figure 2: DBP levels in PER.C6 cells transfected with pcDNA3, pcDNA3wtE2A or pcDNA3ts125E2A

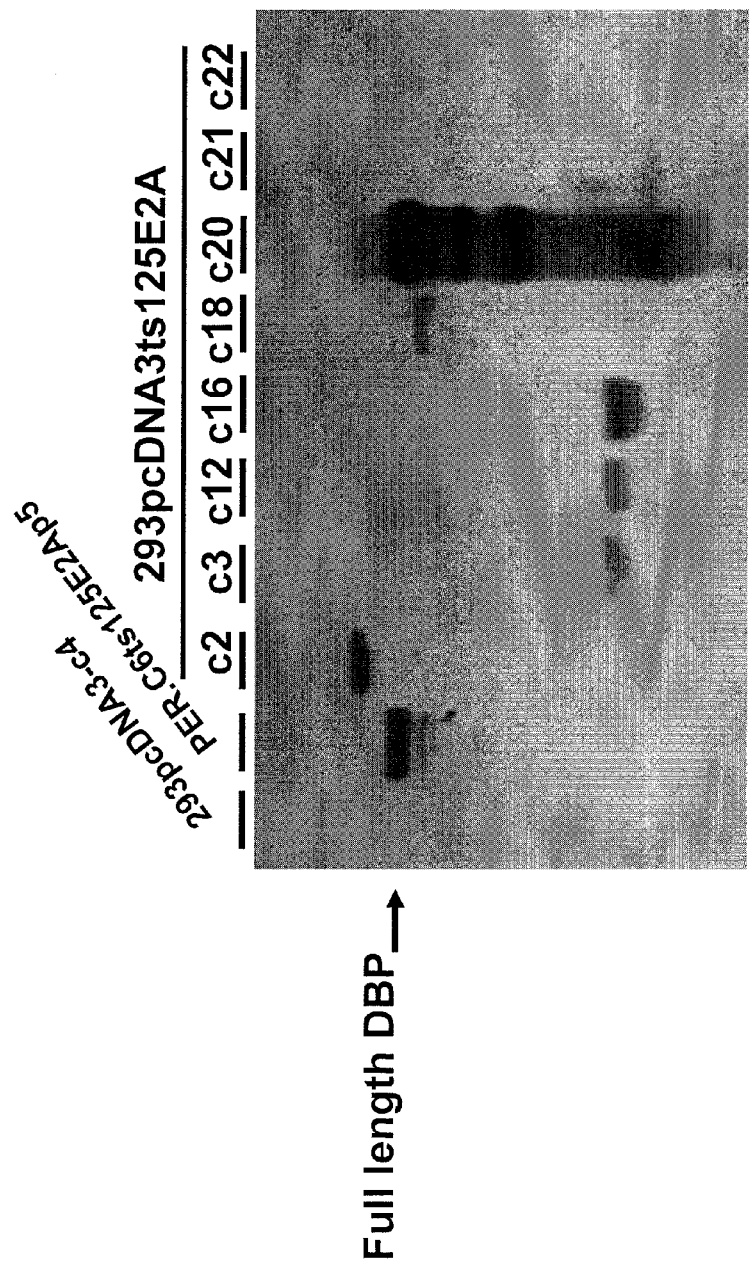
Figure 3: DBP expression in pcDNA3ts125E2A transfected 293 cells

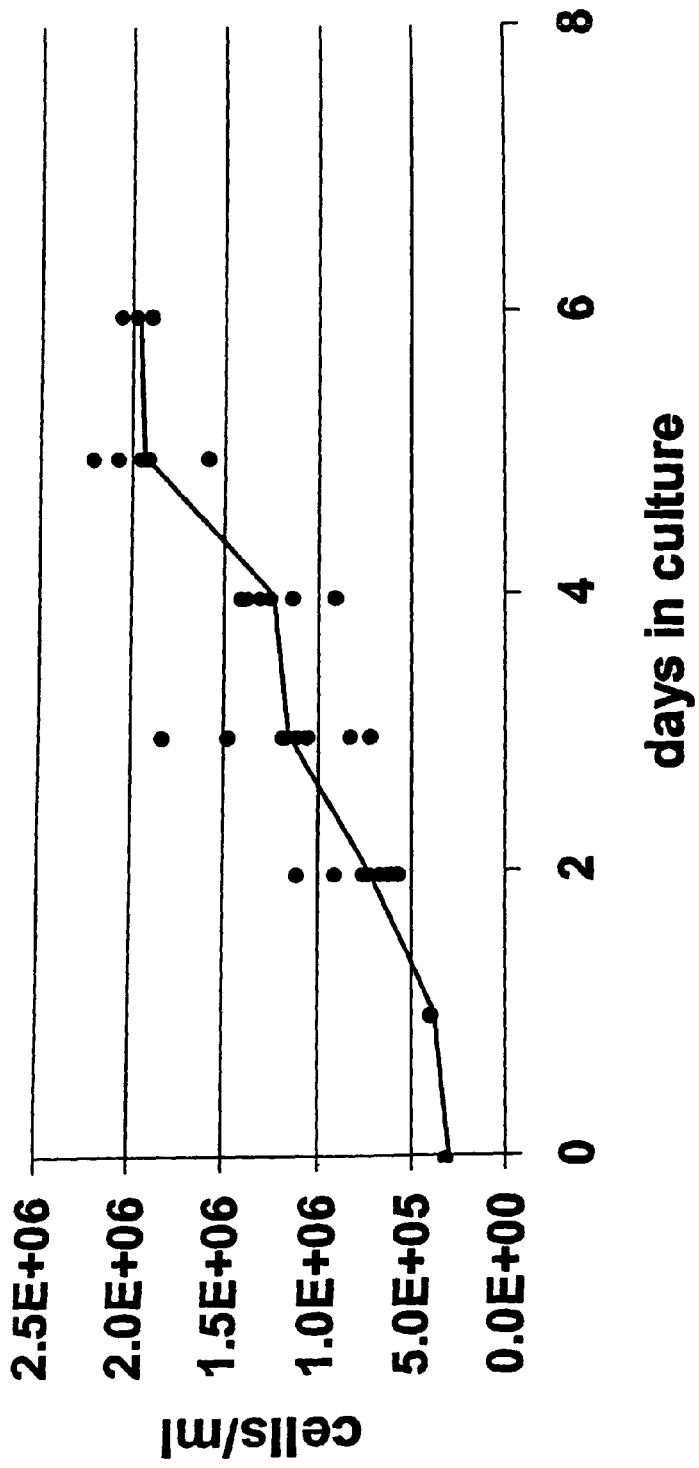
Figure 4: Suspension growth of PER.C6ts125E2A C5-9

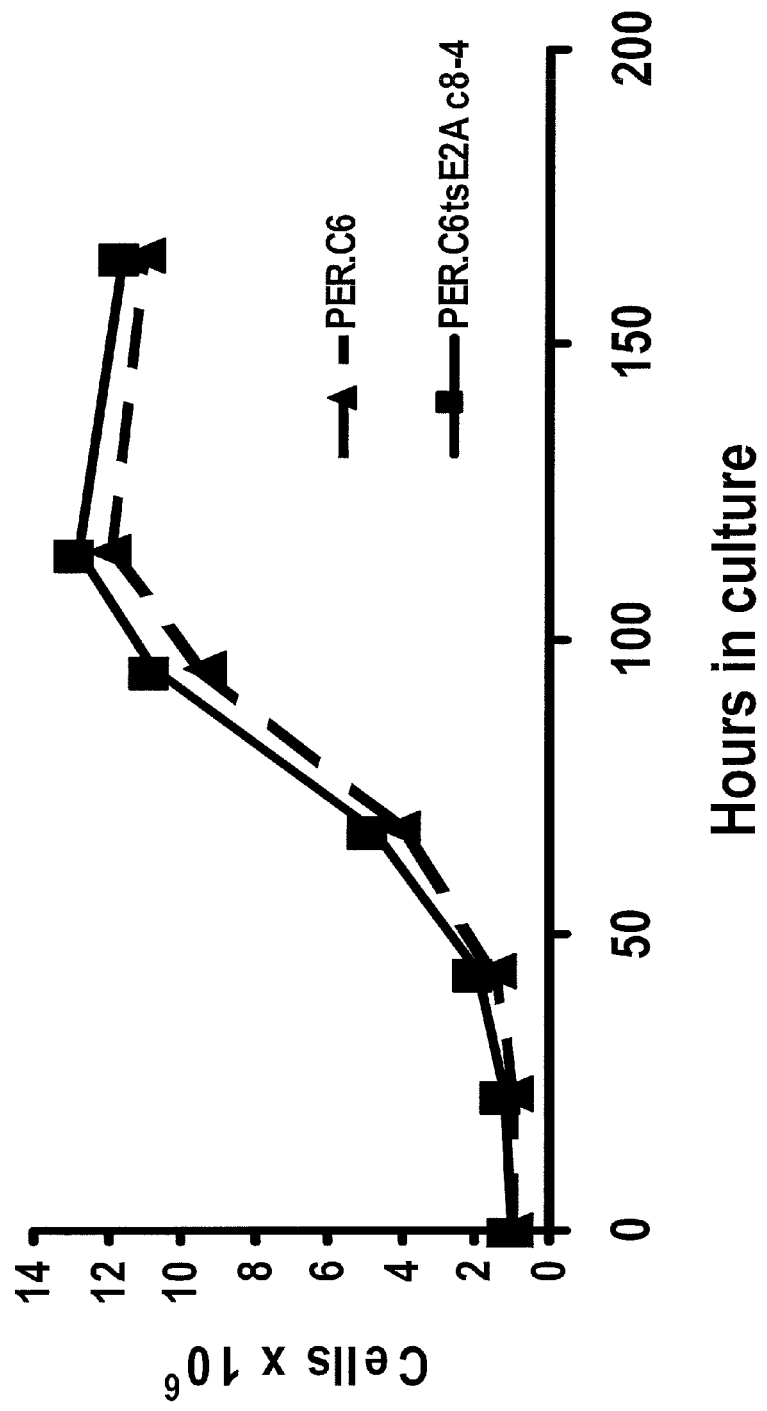

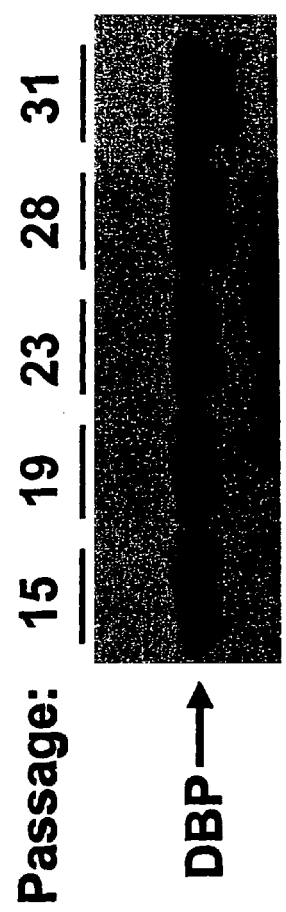
Figure 6: Stability of PER.C6ts125E2A

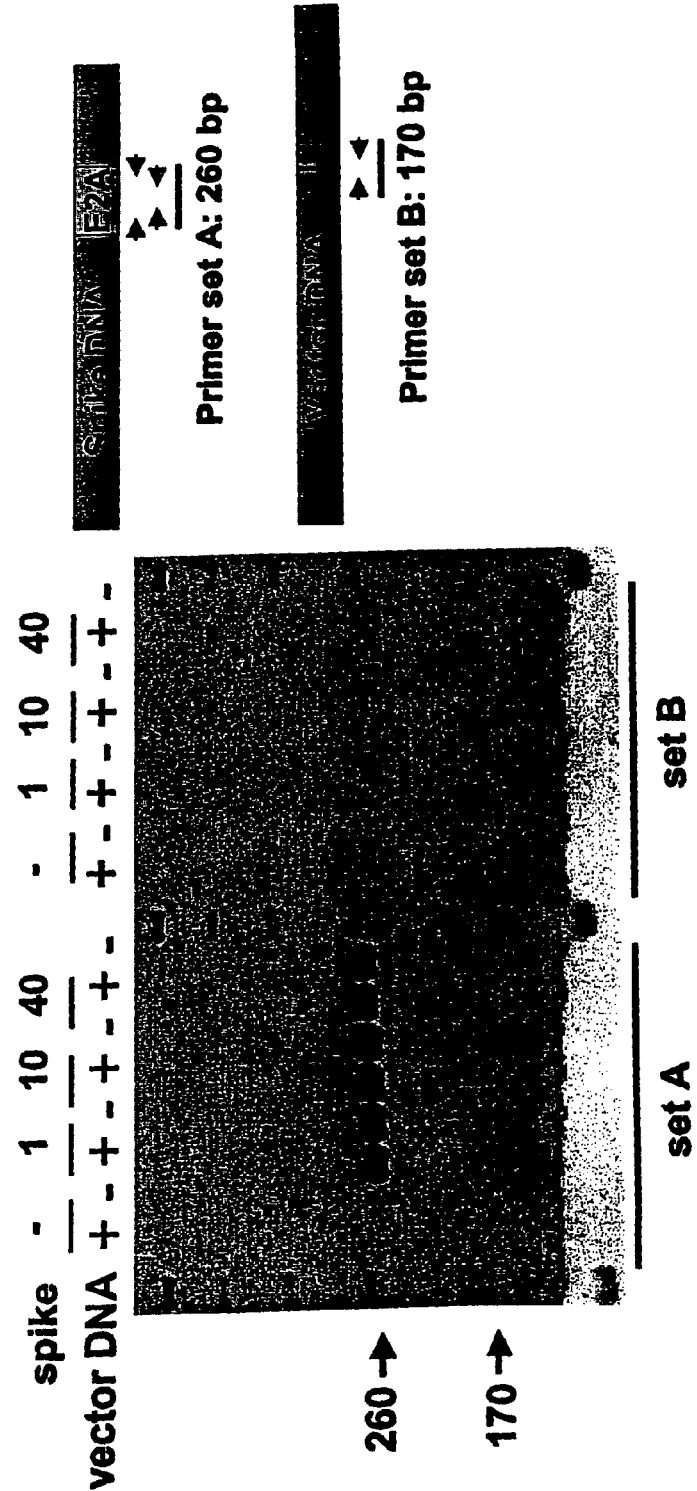
Figure 7: Revertant-Free manufacturing of ΔE1/E2A vectors

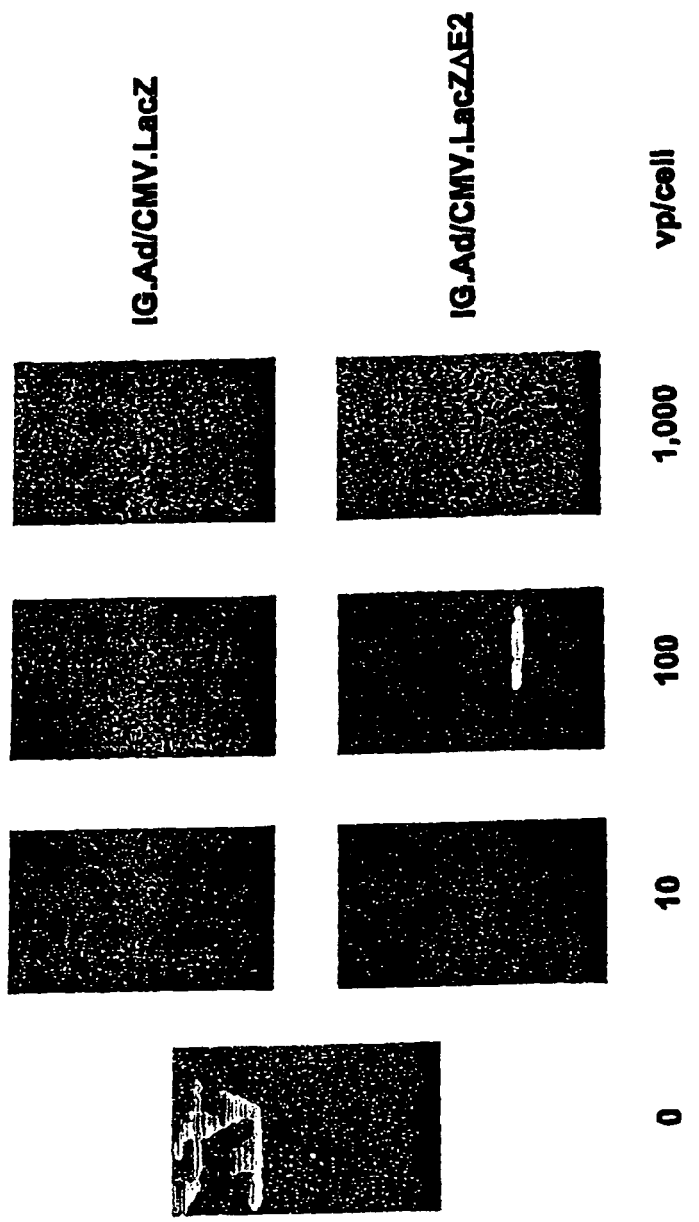
Figure 8: Transduction of Hela cells with IG.Ad/CMV.LacZ and IG.Ad/CMV.LacZΔE2A

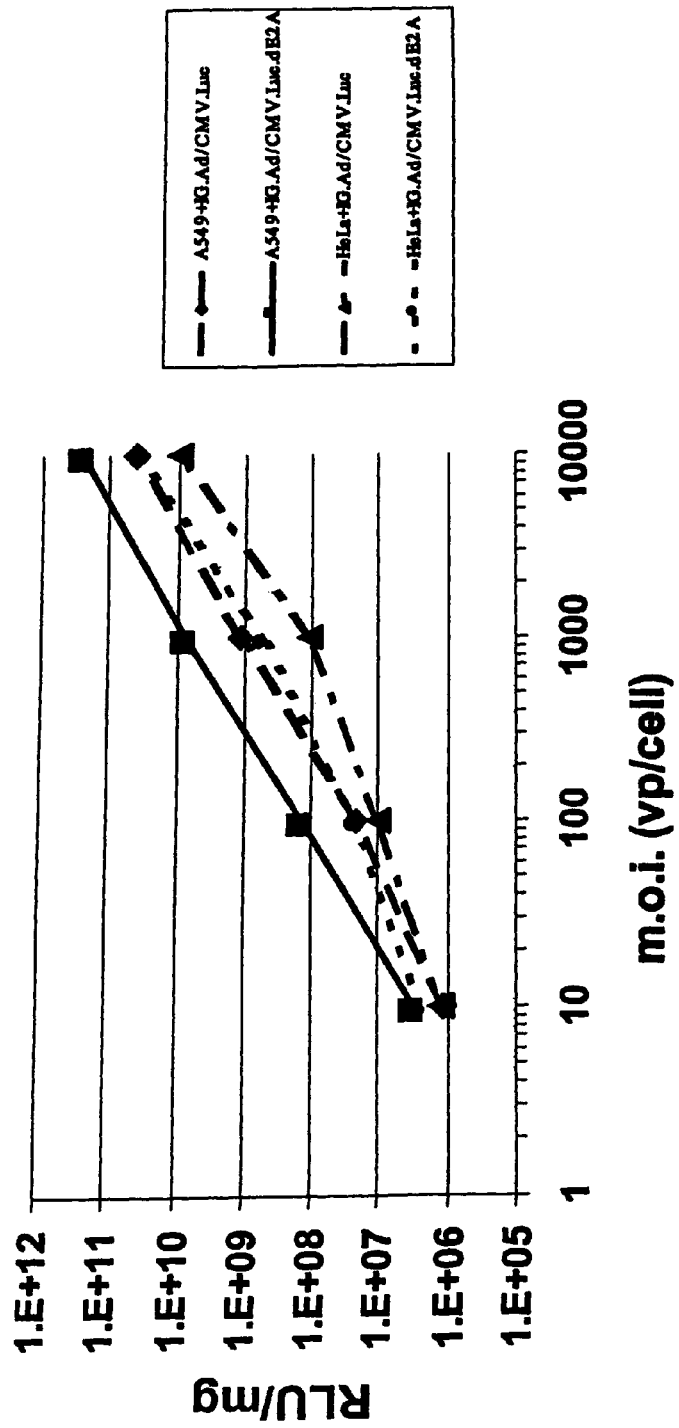
Figure 9: Luciferase activity in infected A549 and HeLa cells

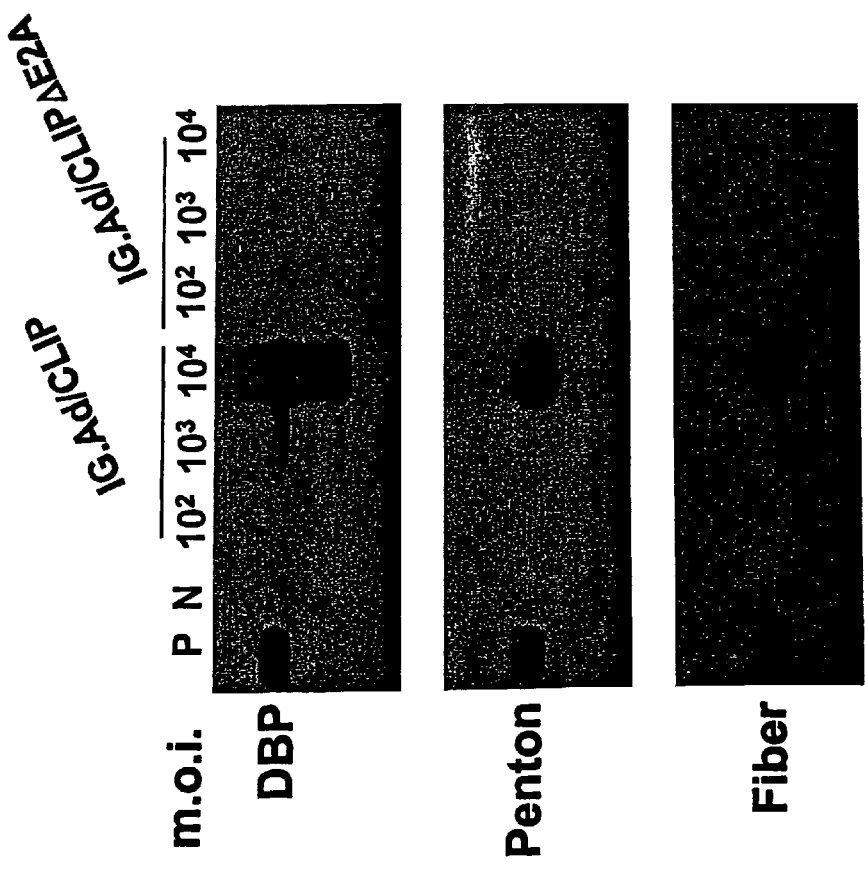
Figure 10: Expression of DBP, Penton and Fiber

MEANS AND METHODS FOR NUCLEIC ACID DELIVERY VEHICLE DESIGN AND NUCLEIC ACID TRANSFER

CROSS-REFERENCE TO RELATED APPLICATIONS

This application is a divisional of U.S. application Ser. No. 10/136,139, filed May 1, 2002, abandoned, which is a continuation of U.S. Ser. No. 09/298,745, now U.S. Pat. No. 6,395,519, which is a continuation-in-part of U.S. patent application Ser. No. 08/793,170, filed Mar. 25, 1997, now U.S. Pat. No. 5,994,128, which is a national stage filing of PCT/NL96/00244, filed Jun. 14, 1996, which claims priority to European Application Nos. EP 95201611.1, filed Jun. 15, 1995, and EP 95201728.3, filed Jun. 26, 1995, the entirety of each of which are incorporated by reference.

TECHNICAL FIELD

The present invention relates to the field of recombinant DNA technology, more in particular to the field of gene therapy. Specifically, the present invention relates to gene therapy using materials derived from adenovirus, in particular human recombinant adenovirus, and relates to novel virus-derived vectors and novel packaging cell lines for vectors based on adenoviruses. Furthermore, this invention also pertains to the screening of replication-competent and revertant E1 and/or E2A adenoviruses from recombinant adenoviruses used in gene therapy.

BACKGROUND

The current generation of adenoviral vectors for gene therapy contains deletions of the early region 1 ("E1"), where new genetic information can be introduced. The E1 deletion renders the recombinant virus replication defective. It was generally thought that E1-deleted vectors would not express any other adenoviral genes, because E1 is reported to trigger the transcription of the other adenoviral genes. It has been shown by us and others that these vectors express several early (e.g., E2A) and late genes (e.g., fiber and penton-base) in the absence of E1. This means that delivery of a therapeutic gene using E1-deleted adenoviral vectors will result in expression of the therapeutic protein and adenoviral proteins. A cytotoxic immune response is evoked against such transduced cells. It has been shown that cytotoxic T-lymphocytes ("CTLs") directed against both the transgene product and products encoded by the vector are activated, following vector administration into immunocompetent animals (Song et al., *Hum. Gene Ther.* 8:1207, 1997; Yang et al., *J. Virol.* 70:7209, 1996). Activated CTLs subsequently eradicate transduced cells from the recipient. Consistent with this, the longevity of transgene expression is significantly extended in immuno-deficient and immuno-compromised animals.

Expression of at least some adenoviral genes in a target cell is at least in part due to background replication of the recombinant adenoviral vector genome and/or background activity of promoters driving the respective adenoviral genes (Yang et al., *Nature Genet.* 7:362, 1994; Lusky et al., *J. Virol.* 72:2022, 1998). As a result of the expression of at least some adenovirus proteins in a target cell in a recipient, an immune response may be mounted against transduced cells. Such an immune response is often not desired, especially when long-term expression of a transgene is aimed for. One mechanism by which adenovirus proteins in a target cell in a recipient may cause the immune system of the recipient to remove the target cell is the following. Proteins encoded by expressed adenovirus genes can be processed into small peptides in a proteosome of the target cell. Peptides produced during this processing can subsequently be presented at the cell surface of the transduced cells in the complex of MHC class-I and □b2-microglobulin molecules. Finally, one or more of the peptides may be recognized as non-self peptides by circulating CTLs whereupon transduced cells can be eradicated from the recipient (reviewed in Ploegh, *Science* 280:248, 1998).

DISCLOSURE OF THE INVENTION

In one aspect, the present invention provides at least in part a solution to the problem of undesired removal of target cells in a recipient.

The present invention also provides, at least in part, a solution for the immune response against viral proteins. To this end, the invention provides improved recombinant adenoviral vectors that, in addition to deletion of E1, are also deleted for the adenoviral early 2A gene ("E2A gene" or "E2A"). The protein encoded by E2A is expressed from recombinant E1-deleted adenoviral vectors. In addition to that, residual expression of E2A from E1-deleted recombinant adenoviral vectors induces the expression of the viral late genes, since DNA binding protein ("DBP") has a positive regulatory effect on the adenovirus major late promoter ("MLP") and, therefore, on the expression of the late genes (Chang et al., *J. Virol.* 64:2103, 1990). Deletion of the E2A gene from the recombinant adenoviral genome will therefore improve the characteristics of recombinant adenoviral vectors. First, deletion of E2A will eliminate the synthesis of DBP. Second, it will inhibit the background replication of the recombinant adenoviral backbone. Third, it will reduce the residual expression of the late genes. Finally, it will increase the capacity of the vector to harbor larger and/or multiple transgenes.

The E2A gene encodes the 72-kDa protein single stranded DBP whose activity is pivotal for the adenovirus DNA replication (reviewed in *The Molecular Repertoire of Adenoviruses II*, Springer-Verlag 1995). Therefore, manufacturing of vectors that are deleted for E2A requires a cell line that complements for the deletion of E2A in the recombinant adenoviral vector. Major hurdles in this approach are:

a) that E2A should be expressed to very high levels and
  b) that constitutive expression of E2A is toxic for cells and, therefore, impossible to achieve (Klessig et al., *Mol. Cell Biol.* 4:1354, 1984).

The current invention, therefore, involves the use of a temperature-sensitive mutant of E2A derived from a temperature-sensitive adenovirus under control of strong viral enhancer sequences, e.g., the cytomegalovirus enhancer for the generation of E2A-complementing cell lines. DBP (ts125E2A) from hAd5ts125 is inactive at 39° C., but is fully active at 32° C. High levels of this protein can be maintained in the new complementing cells of the invention at the non-permissive temperature, until the switch is made to the permissive temperature. The invention also provides means and methods to use the complementing cell line, comprising E2A, tsE2A, or both E1 and tsE2A, for the generation of E2A- or E1- and E2A-deleted adenoviral vectors. The invention also involves inducible expression of E2A or tsE2A.

The invention also provides new cell lines that complement for E2A or for both the E1 and the E2A deletion in the vector. The invention also provides new recombinant adenoviral vectors deleted for E2A or both E1 and E2A.

BRIEF DESCRIPTION OF THE FIGURES

FIG. 1 depicts the temperature dependent growth of PER.C6. PER.C6 cells were cultured in Dulbecco's Modified Eagle Medium supplemented with 10% Fetal Bovine Serum (FBS, Gibco BRL) and 10 mM $MgCl_2$ in a 10% $CO_2$ atmosphere at either 32° C., 37° C. or 39° C. At day 0, a total of $1 \times 10^6$ PER.C6 cells were seeded per 25 $cm^2$ tissue culture flask (Nunc) and the cells were cultured at either 32° C., 37° C. or 39° C. At each of days 1 through 8, cells were counted. The growth rate and the final cell density of the PER.C6 culture at 39° C. are comparable to that at 37° C. The growth rate and final density of the PER.C6 culture at 32° C. were slightly reduced as compared to that at 37° C. or 39° C.

FIG. 2 depicts DBP levels in PER.C6 cells transfected with pcDNA3, pcDNA3wtE2A or pcDNA3ts125E2A. Equal amounts of whole-cell extract were fractionated by SDS-PAGE on 10% gels. Proteins were transferred onto Immobilon-P membranes and DBP protein was visualized using the aDBP monoclonal B6 in an ECL detection system. All of the cell lines derived from the pcDNA3ts125E2A transfection express the 72-kDa E2A-encoded DBP protein (left panel, lanes 4 to 14; middle panel, lanes 1 to 13; right panel, lanes 1 to 12). In contrast, the only cell line derived from the pcDNAwtE2A transfection did not express the DBP protein (left panel, lane 2). No DBP protein was detected in extract from a cell line derived from the pcDNA3 transfection (left panel, lane 1), which serves as a negative control. Extract from PER.C6 cells transiently transfected with pcDNA3ts125 (left panel, lane 3) served as a positive control for the Western blot procedure. These data confirm that constitutive expression of wtE2A is toxic for cells and that using the ts125 mutant of E2A can circumvent this toxicity.

FIG. 3 depicts DBP expression in pcDNA3ts125E2A-transfected 293 cells. Equal amounts of whole-cell extract were fractionated by SDS-PAGE on 10% gels. Proteins were transferred onto Immobilon-P membranes and DBP protein was visualized using the aDBP monoclonal B6 in an ECL detection system. Clone 20 (lane 8) from the pcDNA3ts125E2A-transfected 293 cells expressed the full-length ts125E2A encoded 72-kDa DBP. No E2A encoded DBP was detected in the extract from a cell line (clone 4) derived from the pcDNA3-transfected 293 cells (lane 1), which serves as a negative control. Extract from PER.C6 cells stably expressing ts125E2A encoded DBP (polyclonal cell line 5) (lane 2) served as a positive control for the Western blot procedure. The other 293 clones either did not express ts125E2A encoded DBP (clones 21 and 22, lanes 9 and 10, respectively) or expressed aberrant products running with a faster (clones 3, 12, 16 and 18, lanes 4 to 7) or slower (clone 2, lane 3) mobility in SDS/PAGE.

FIG. 4 depicts suspension growth of PER.C6ts125E2A cell line c5-9. PER.C6ts125E2Ac5-9 cells were seeded in a 125 ml tissue culture Erlenmeyer at a seeding density of $3 \times 10^5$ cells per ml in a total volume of 20 ml serum-free medium. Cells were further cultured at 125 RPM on an orbital shaker at 39° C. in a 10% $CO_2$ atmosphere. Cells were counted at each of days 1 through 6. The mean growth curve from eight cultures is shown. PER.C6ts125E2Ac5-9 performs well in serum-free suspension culture. The maximum cell density of approximately $2 \times 10^6$ cells per ml is reached within five days of culture.

FIG. 5 depicts growth curve PER.C6 and PER.C6tsE2A. PER.C6 cells or PER.C6ts125E2A (c8-4) cells were cultured at 37° C. or 39° C., respectively. At day 0, a total of $1 \times 10^6$ cells was seeded per 25 $cm^2$ tissue culture flask. At the indicated time points, cells were counted. The growth of PER.C6 cells at 37° C. is comparable to the growth of PER.C6ts125E2A c8-4 at 39° C. This shows that constitutive over-expression of ts125E2A has no adverse effect on the growth of cells at the non-permissive temperature of 39° C.

FIG. 6 depicts stability of PER.C6ts125E2A. For several passages, the PER.C6ts125E2A cell line clone 8-4 was cultured at 39° C. in medium without G418. Equal amounts of whole-cell extract from different passage numbers were fractionated by SDS-PAGE on 10% gels. Proteins were transferred onto Immobilon-P membranes and DBP protein was visualized using the aDBP monoclonal B6 in an ECL detection system. The expression of ts125E2A encoded DBP is stable for at least 16 passages, which is equivalent to approximately 40 cell doublings. No decrease in DBP levels was observed during this culture period, indicating that the expression of ts125E2A is stable, even in the absence of G418 selection pressure.

FIG. 7 depicts revertant-free manufacturing of DE1/E2A vectors. The recombinant adenoviral vector DNA was screened for reversion of the E2A-deleted phenotype by PCR. As shown in the left panel, E2A sequences were amplified from the DNA samples (+) and control samples (−) spiked with both 1, 10 and 40 molecules using primer set A, as evidenced by the amplification of a 260 base pair ("bp") DNA fragment. In contrast, no E2A sequences were amplified from the non-spiked samples, showing that reversion of the E2A-deleted did not occur. As shown in the right panel, the PCR reactions with primer set B yielded the expected DNA fragment of 169 bp in the samples containing the recombinant adenoviral vector DNA (+). From the negative control samples containing the water instead of DNA (−), no DNA fragment of 169 bp was amplified. These data show that elimination of overlap between adenoviral sequences in the vector and cell line prevents reversion of the E2A-deleted phenotype.

FIG. 8 depicts transduction of HeLa cells with IG.Ad/CMV.LacZ and IG.Ad/CMV.LacZDE2A. HeLa cells were infected with a multiplicity of infection ("m.o.i.") of either 0, 10, 100 or 1000 viral particles IG.Ad/CMV.LacZ or IG.Ad/CMV.LacZDE2A per cell. Forty-eight hours post infection, cells were stained with X-gal solution. IG.Ad/CMV.LacZDE2A transduced HeLa cells stained at least as good as did IG.Ad/CMV.LacZ, at all m.o.i.s.

FIG. 9 depicts luciferase activity in infected A549 and HeLa cells. HeLa and A549 cells were infected with a m.o.i. of either 0, 10, 100, 1,000 or 10,000 virus particles ("vp") IG.Ad/CLIP.Luc or IG.Ad/CLIP.LucDE2A per cell. Two days post infection, cells were lysed and the luciferase activity was determined. Both the IG.Ad/CLIP.LucDE2A infected HeLa and A549 cells produce more luciferase enzyme than the IG.Ad/CLIP.Luc infected HeLa and A549 and HeLa cells, at all m.o.i.s tested.

FIG. 10 depicts the expression of DBP, Penton and Fiber. A549 cells were infected with a m.o.i. of either 0, 100, 1,000 or 10,000 vp/cell IG.Ad/CLIP or IG.Ad.CLIPDE2A. Seventy-two hours post infection, cell extracts were prepared and equal amounts of whole cell extract were fractionated by SDS-PAGE on 10% gels. The proteins were visualized with the aDBP monoclonal B6, the polyclonal a-Penton base Ad2-Pb571 or the polyclonal a-knob domain of fiber E641/3, using an ECL detection system. Cells infected with IG.Ad.CLIP express both E2A encoded DBP, Penton base and Fiber proteins. The proteins co-migrate with the respective proteins in the positive control (lane P, extract from PER.C6 cells infected with IG.Ad.CLIP harvested at starting CPE). In contrast, no DBP, penton-base or fiber was detected in the non-infected A549 cells or cells infected with IG.Ad.CLIPDE2A. These data show that deletion of the E2A gene did not only eliminate residual DBP expression, but also the residual expression of the late adenoviral proteins penton-base and fiber.

DETAILED DESCRIPTION OF THE INVENTION

According to a presently preferred embodiment of the invention, a cell according to the invention is capable of at least, in part, complementing adenovirus E2A function of an adenovirus defective in E2A function. Such a cell includes a nucleic acid-encoding adenovirus E2A or a functional part, derivative and/or analogue thereof, integrated into the genome of the cell. Preferably, the cell has E2A nucleic acid derived from a temperature-sensitive adenovirus such as but not limited to adenovirus ts125. More preferably, such a cell further includes a nucleic acid-encoding adenovirus E1-region proteins or a functional part, derivative and/or analogue thereof. Such a cell could be derived from the "PER.C6" cell line (commercially available from IntroGene, bv, and deposited, under ECACC deposit accession number 96022940 under the provisions of the Budapest Treaty with the Centre for Applied Microbiology and Research Authority (European Collection of Animal Cell Cultures), Porton Down, Salisbury, Wiltshire SP4, OJG, United Kingdom, an International Depository Authority, in accordance with the Budapest Treaty, on Feb. 29, 1996.

The invention also includes a method for producing an adenovirus particle containing an adenovirus vector with a functional deletion of E2A. Such a method involves providing a cell as previously described with the functionally deleted adenovirus vector, culturing the cell, and harvesting the virus particle. In such a method, the functional deletion can comprise a deletion of at least part of the nucleic acid-encoding E2A. In such a method, the nucleic acid-encoding adenovirus E2A in the genome of the cell preferably has no sequence overlap with the vector which leads to replication-competent adenovirus and/or to the formation of an adenovirus vector comprising E2A function. In the method, the adenovirus vector preferably further comprises a functional deletion of E1-region-encoding nucleic acid, comprising providing one of the previously described cells with the adenovirus vector, culturing the cell and harvesting the virus particle. In such a method, the nucleic acid-encoding adenovirus E1-region preferably does not comprise sequence overlap with the vector which leads to replication-competent adenovirus and/or to the formation of an adenovirus vector comprising an E1 function. Furthermore, in the method, the adenovirus vector further comprises at least one nucleic acid of interest.

The invention also includes an adenovirus vector comprising a functional deletion of adenovirus E2A. Such a functional deletion is preferably a deletion of at least part of the nucleic acid-encoding E2A. The deletion may encompass the entire coding region of E2A. Such an adenovirus vector preferably includes a deletion corresponding to a deletion of nucleotides 22443 to 24032 in adenovirus 5. The deletion can include a deletion of nucleic acid-encoding E1-region proteins. The deletion of nucleic acid-encoding E1-region proteins can comprise a deletion corresponding to a deletion of nucleotides 459 to 3510 in adenovirus 5. Again, the adenovirus vector preferably further includes at least one nucleic acid of interest.

An adenovirus vector according to the invention can, but does not necessarily, also comprise at least a deletion of a region which in adenovirus 5 corresponds to nucleotides 22418-24037 or a deletion of a region which in adenovirus 5 corresponds to nucleotides 22443-24032. Such vectors can further comprise at least nucleic acid which in adenovirus 5 corresponds to nucleotides 3534-22347 and/or nucleotides 24060 until the right ITR or at least 3534-22417 and/or 24038 until the right ITR or at least nucleic acid which in adenovirus 5 corresponds to nucleotides 3534-22442 and/or nucleotides 24033 until the right ITR.

The invention also includes preparations of adenovirus vector containing adenovirus particles wherein the adenovirus vector comprises a functional deletion of E2A. Such an adenovirus vector preferably further includes a deletion of nucleic acid-encoding E1-region proteins, and may be free of adenovirus vectors comprising E2A function. In such a case, the preparation may be free of adenovirus vectors comprising nucleic acid encoding a functional E2A, or a functional part, derivative and/or analogue thereof. The preparation is preferably free of adenovirus vectors comprising nucleic acid-encoding E1-region proteins or parts, derivatives and/or analogues thereof.

The invention also includes a method for providing cells of an individual with a nucleic acid of interest, without risk of administering simultaneously a replication-competent adenovirus vector, comprising administering the individual one of the previously described preparations.

The invention is further described by the use of the following illustrative Examples.

EXAMPLE I

Generation of Producer Cell Lines for the Production of Recombinant Adenoviral Vectors Deleted in E1 and E2A or E1 and E2A Here is described the generation of cell lines for the production of recombinant adenoviral vectors that are deleted in E1 and E2A. The producer cell lines complement for the E1 and E2A deletion from recombinant adenoviral vectors in trans by constitutive expression of the E1 and E2A genes, respectively. The pre-established Ad5-E1 transformed human embryo retinoblast cell line PER.C6 (commercially available from IntroGene, bv (now Crucell, NV) of Leiden, NL, see also, International Patent Appln. WO 97/00326) and Ad5 transformed human embryo kidney cell line 293 (Graham et al., *J. Gen. Virol*. 36:59, 1977) were further equipped with E2A expression cassettes.

The adenoviral E2A gene encodes a 72 kDa DBP which has a high affinity for single stranded DNA. Because of its function, constitutive expression of DBP is toxic for cells. The ts125E2A mutant encodes a DBP which has a Pro→Ser substitution of amino acid 413 (van der Vliet, *J. Virol*. 15:348, 1975). Due to this mutation, the ts125E2A encoded DBP is fully active at the permissive temperature of 32° C., but does not bind to ssDNA at the non-permissive temperature of 39° C. This allows the generation of cell lines that constitutively express E2A, which is not functional and is not toxic at the non-permissive temperature of 39° C. Temperature-sensitive E2A gradually becomes functional upon temperature decrease and becomes fully functional at a temperature of 32° C., the permissive temperature.

A. Generation of Plasmids Expressing the Wild-Type E2A- or Temperature-Sensitive ts125E2A Gene.

pcDNA3wtE2A: The complete wild-type E2A coding region was amplified from the plasmid pBR/Ad.Bam-rITR (ECACC deposit P97082122) with the primers DBPpcr1 and DBPpcr2 using the Expand™ Long Template PCR system according to the standard protocol of the supplier (Boehringer Mannheim). The PCR was performed on a Biometra TRIO THERMOBLOCK, using the following amplification program: 94° C. for 2 minutes, 1 cycle; 94° C. for 10 seconds+51° C. for 30 seconds+68° C. for 2 minutes, 1 cycle; 94° C. for 10 seconds+58° C. for 30 seconds+68° C. for 2 minutes, 10 cycles; 94° C. for 10 seconds+58° C. for 10 seconds+58° C.

for 30 seconds+68° C. for 2 minutes with 10 seconds extension per cycle, 20 cycles; 68° C. for 5 minutes, 1 cycle. The primer DBPpcr1: CGGGATCCG CCA CCA TGG CCA GTC GGG AAG AGG $\overline{AG}$ (5' to 3') (SEQ ID NO:1) contains a unique BamHI restriction site (underlined) 5' of the Kozak sequence (italic) and start codon of the E2A coding sequence. The primer DBPpcr2: CGGAATTCT TAA AAA TCA AAG GGG TTC TGC CGC (5' to 3') (SEQ ID NO:2) contains a unique EcoRI restriction site (underlined) 3' of the stop codon of the E2A coding sequence. The bold characters refer to sequences derived from the E2A coding region. The PCR fragment was digested with BamHI/EcoRI and cloned into BamHI/EcoRI digested pcDNA3 (Invitrogen), giving rise to pcDNA3wtE2A.

pcDNA3tsE2A: The complete ts125E2A-coding region was amplified from DNA isolated from the temperature-sensitive adenovirus mutant H5ts125 (Ensinger et al., *J. Virol.* 10:328, 1972; van der Vliet et al., *J. Virol.* 15:348, 1975). The PCR amplification procedure was identical to that for the amplification of wtE2A. The PCR fragment was digested with BamHI/EcoRI and cloned into BamHI/EcoRI digested pcDNA3 (Invitrogen), giving rise to pcDNA3tsE2A. The integrity of the coding sequence of wtE2A and tsE2A was confirmed by sequencing.

B. Growth Characteristics of Producer Cells for the Production of Recombinant Adenoviral Vectors Cultured at 32°, 37° and 39° C.

PER.C6 cells were cultured in Dulbecco's Modified Eagle Medium ("DMEM," Gibco BRL) supplemented with 10% FBS and 10 mM $MgCl_2$ in a 10% $CO_2$ atmosphere at either 32° C., 37° C. or 39° C. At day 0, a total of $1\times10^6$ PER.C6 cells were seeded per 25 $cm^2$ tissue culture flask (Nunc) and the cells were cultured at either 32° C., 37° C. or 39° C. At each of days 1 through 8, cells were counted. FIG. 1 shows that the growth rate and the final cell density of the PER.C6 culture at 39° C. are comparable to that at 37° C. The growth rate and final density of the PER.C6 culture at 32° C. were slightly reduced as compared to that at 37° C. or 39° C. No significant cell death was observed at any of the incubation temperatures. Thus PER.C6 performs very well both at 32° C. and 39° C., the permissive and non-permissive temperature for ts125E2A, respectively.

C. Transfection of PER.C6 and 293 with E2A Expression Vectors; Colony Formation and Generation of Cell Lines.

One day prior to transfection, $2\times10^6$ PER.C6 cells were seeded per 6 cm tissue culture dish (Greiner) in DMEM, supplemented with 10% FBS and 10 mM $MgCl_2$ and incubated at 37° C. in a 10% $CO_2$ atmosphere. The next day, the cells were transfected with 3, 5 or 8 μg of either pcDNA3, pcDNA3wtE2A or pcDNA3tsE2A plasmid DNA per dish, using the LipofectAMINE PLUS™ Reagent Kit according to the standard protocol of the supplier (Gibco BRL), except that the cells were transfected at 39° C. in a 10% $CO_2$ atmosphere. After the transfection, the cells were constantly kept at 39° C., the non-permissive temperature for ts125E2A. Three days later, the cells were put on DMEM, supplemented with 10% FBS, 10 mM $MgCl_2$ and 0.25 mg/ml G418 (Gibco BRL) and the first G418 resistant colonies appeared at 10 days post transfection. As shown in Table 1, there was a dramatic difference between the total number of colonies obtained after transfection of pcDNA3 (~200 colonies) or pcDNA3tsE2A (~100 colonies) and pcDNA3wtE2A (only four colonies). These results indicate that the constitutive expression of E2A is toxic and the toxicity of constitutively expressed E2A can be overcome by using a temperature-sensitive mutant of E2A (ts125E2A) and culturing of the cells at the non-permissive temperature of 39° C.

TABLE 1

Number of colonies after transfection of PER.C6 with E2A expression vectors:

| plasmid | number of colonies | cell lines established |
|---|---|---|
| pcDNA3 | ~200 | 4/4 |
| PcDNA3wtE2A | 4 | 1/4 |
| PcDNA3tsE2A | ~100 | 37/45 |

PER.C6 cells were transfected with either pcDNA3, pcDNA3wtE2A or pcDNA3wtE2A and cultured in selection medium containing 0.25 mg/ml G418 at 39° C. All colonies (4/4) picked from the pcDNA3 transfection and 82% (37/45) of the colonies from the pcDNA3tsE2A transfection were established to stable cell lines. In contrast, only 25% (¼) of the colonies from the pcDNA3wtE2A transfection could be established to a cell line.

From each transfection, a number of colonies was picked by scraping the cells from the dish with a pipette. The detached cells were subsequently put into 24-well tissue culture dishes (Greiner) and cultured further at 39° C. in a 10% $CO_2$ atmosphere in DMEM, supplemented with 10% FBS, 10 mM $MgCl_2$ and 0.25 mg/ml G418. As shown in Table 1, 100% of the pcDNA3-transfected colonies (4/4) and 82% of the pcDNA3tsE2A-transfected colonies (37/45) were established to stable cell lines (the remaining eight pcDNA3tsE2A-transfected colonies grew slowly and were discarded). In contrast, only one pcDNA3wtE2A-transfected colony could be established. The other three died directly after picking.

Next, the E2A expression levels in the different cell lines were determined by Western blotting. The cell lines were seeded on 6-well tissue culture dishes and sub-confluent cultures were washed twice with PBS (NPBI) and lysed and scraped in RIPA (1% NP-40, 0.5% sodium deoxycholate and 0.1% SDS in PBS, supplemented with 1 mM phenylmethyl-sulfonylfluoride and 0.1 mg/ml trypsin inhibitor). After 15 minutes incubation on ice, the lysates were cleared by centrifugation. Protein concentrations were determined by the Bio-Rad protein assay, according to standard procedures of the supplier (BioRad). Equal amounts of whole-cell extract were fractionated by SDS-PAGE on 10% gels. Proteins were transferred onto Immobilon-P membranes (Millipore) and incubated with the aDBP monoclonal antibody B6 (Reich et al., *Virology* 128:480, 1983). The secondary antibody was a horseradish-peroxidase-conjugated goat anti mouse antibody (BioRad). The Western blotting procedure and incubations were performed according to the protocol provided by Millipore. The complexes were visualized with the ECL detection system according to the manufacturer's protocol (Amersham). FIG. 2 shows that all of the cell lines derived from the pcDNA3tsE2A transfection express the 72-kDa E2A protein (left panel, lanes 4 to 14; middle panel, lanes 1 to 13; right panel, lanes 1 to 12). In contrast, the only cell line derived from the pcDNAwtE2A transfection did not express the E2A protein (left panel, lane 2). No E2A protein was detected in extract from a cell line derived from the pcDNA3 transfection (left panel, lane 1), which serves as a negative control. Extract from PER.C6 cells transiently transfected with pcDNA3ts125 (left panel, lane 3) served as a positive control for the Western blot procedure. These data confirm that constitutive expression of wtE2A is toxic for cells and that using the ts125 mutant of E2A can circumvent this toxicity.

In contrast to PER.C6 cells, the culturing of 293 cells at 39° C. is troublesome. Therefore, the transfection of 293 cells with either pcDNA3, pcDNA3wtE2A or pcDNA3tsE2A was performed at 37° C. in an atmosphere of 10% $CO_2$, a semi-permissive temperature for ts125E2A encoded DBP. A day prior to transfection, 293 cells were seeded in DMEM, supplemented with 10% FBS and 10 mM $MgCl_2$, at a density of $3.6 \times 10^5$ cells per 6 cm tissue culture dish (Greiner). Five hours before transfection, cells received fresh medium. Cells were transfected with 7.2 µg of either pcDNA3, pcDNA3wtE2A or pcDNA3tsE2A plasmid DNA using the Calcium Phosphate Transfection System according to the standard protocol of the supplier (Gibco BRL). Two days post transfection, cells were put on selection medium, i.e., DMEM supplemented with 10% FBS, 10 mM $MgCl_2$ and 0.1 mg/ml G418. The first colonies appeared at day 12 post transfection. As shown in Table 2, the total number of colonies obtained after transfection of pcDNA3 (~100 colonies) or pcDNA3tsE2A (~25 colonies) was significantly higher than that obtained after transfection of pcDNA3wtE2A (only two colonies). A total of 22 clones from the pcDNA3tsE2A transfection were picked by scraping the cells from the dish with a pipette. The detached cells were subsequently put into 96-well tissue culture dishes (Greiner) and cultured further at 37° C. in a 10% $CO_2$ atmosphere in DMEM, supplemented with 10% FBS, 10 mM $MgCl_2$ and 0.1 mg/ml G418. Sixteen out of the 22 picked colonies could be established as cell lines (the six remaining colonies grew badly and were discarded).

TABLE 2

Number of colonies after transfection of 293 with E2A expression vectors:

| plasmid | number of colonies |
| --- | --- |
| pcDNA3 | ~100 |
| PcDNA3wtE2A | 2 |
| PcDNA3tsE2A | 25 |

Selection of colonies derived from 293 cells transfected with E2A expression cassettes. Cell line 293 was transfected with either pcDNA3, pcDNA3wtE2A or pcDNA3wtE2A and cultured in selection medium containing 0.1 mg/ml G418 at 37° C.

Next, the E2A expression level in 8 different cell lines was determined by Western blotting. The cell lines were seeded on 6-well tissue culture dishes and sub-confluent cultures were washed twice with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the BioRad protein assay, according to standard procedures of the supplier (BioRad). Equal amounts of whole-cell extract were fractionated by SDS-PAGE on 10% gels. Proteins were transferred onto Immobilon-P membranes (Millipore) and incubated with the aDBP monoclonal antibody B6 (Reich et al., Virology 128:480, 1983). The secondary antibody was a horseradish-peroxidase-conjugated goat anti mouse antibody (BioRad). The Western blotting procedure and incubations were performed according to the protocol provided by Millipore. The complexes were visualized with the ECL detection system according to the manufacturer's protocol (Amersham). FIG. 3 shows, that, in contrast to the PER.C6tsE2A cell lines, only clone 20 (lane 8) from the pcDNA3tsE2A-transfected 293 cells expressed the full-length ts125E2A encoded 72-kDa DBP. No E2A encoded DBP was detected in extract from a cell line (clone 4) derived from the pcDNA3-transfected 293 cells (lane 1), which serves as a negative control. Extract from PER.C6 cells stably expressing ts125E2A encoded DBP (polyclonal cell line 5) (lane 2) served as a positive control for the Western blot procedure. The other 293 clones either did not express ts125E2A encoded DBP (clones 21 and 22, lanes 9 and 10 respectively) or expressed aberrant products running with a faster (clones 3, 12, 16 and 18 lanes 4 to 7) or slower (clone 2, lane 3) mobility in SDS/PAGE. These results show that generation of E2A-complementing cell lines by using temperature-sensitive mutants of E2A is not specific for PER.C6 cells, but that it applies to eukaryotic cells in general (e.g., 293 cells). In addition, the 293 data show that keeping the temperature-sensitive E2A encoded DBP as inactive as possible is crucial for easy generation of such cell lines. The 293 cell lines were generated at an intermediate temperature of 37° C., a temperature at which ts125E2A encoded DBP is only partially inactivated. This explains the high number of cell lines expressing aberrant DBP products.
D. Complementation of E2A Deletion in Adenoviral Vectors on PER.C6 and 293 Cells Constitutively Expressing Full-length ts125E2A Encoded DBP.

The adenovirus Ad5.d1802 is an Ad 5-derived vector deleted for the major part of the E2A coding region and does not produce functional DBP (Rice et al., J. Virol. 56:767, 1985). Ad5.d1802 was used to test the E2A trans-complementing activity of PER.C6 cells constitutively expressing ts125E2A. Parental PER.C6 cells or PER.C6tsE2A clone 3-9 were cultured in DMEM, supplemented with 10% FBS and 10 mM $MgCl_2$ at 39° C. and 10% $CO_2$ in 25 $cm^2$ flasks and either mock infected or infected with Ad5.d1802 at an m.o.i. of 5. Subsequently, the infected cells were cultured at 32° C. and cells were screened for the appearance of a cytopathic effect (CPE) as determined by changes in cell morphology and detachment of the cells from the flask. Table 3 shows that full CPE appeared in the Ad5.d1802 infected PER.C6tsE2A clone 3-9 within two days. No CPE appeared in the Ad5.d1802 infected PER.C6 cells or the mock infected cells. These data show that PER.C6 cells constitutively expressing ts125E2A complement in trans for the E2A deletion in the Ad5.d1802 vector at the permissive temperature of 32° C.

These cells are therefore suitable for production of recombinant adenoviral vector that are deficient for functional E2A.

TABLE 3

Complementation of E2A deletion in adenoviral vectors on PER.C6 cells and PER.C6 cells constitutively expressing temperature-sensitive E2A.

| | 32° C. day 2 |
| --- | --- |
| PER.C6 mock | — |
| PER.C6 dl802 | — |
| PER.C6ts125c3-9 mock | — |
| PER.C6ts125c3-9 dl802 | Full CPE |

Parental PER.C6 cells or PER.C6ts125E2A clone 3-9 were infected with Ad5.d1802, an Ad5 adenovirus deleted for the E2A gene, at an m.o.i. of 5. Subsequently, the infected cells were cultured at 32° C. and cells were screened for the appearance of a cytopathic effect (CPE) as determined by changes in cell morphology and detachment of the cells from the flask.

The 293tsE2A clones c2, c16, c18 and c20 and the 293pcDNA3-clone c4 were tested for their E2A trans-complementing activity as follows. The cell lines were cultured in DMEM, supplemented with 10% FBS and 10 mM $MgCl_2$ at 39° C. and 10% $CO_2$ in 6-well plates and either mock infected or infected with IG.Ad.CLIP.Luc (see below) at an m.o.i. of 10. Subsequently, the infected cells were cultured at either 32° C. or 39° C. and cells were screened for the appearance of a cytopathic effect (CPE) three days post infection, as determined by changes in cell morphology and detachment of the cells from the flask. Table 4 shows that no CPE appeared in the control cell line 293pcDNA3-c4. Moreover, the cell lines expressing aberrant forms of DBP either failed to complement this vector (clones 16 and 18) or were intermediate in the trans-complementing ability (clone 2). Only the 293 cell line expressing full-length ts125E2A encoded DBP (i.e., clone 20) fully complemented for the E2A deletion in the vector IG.Ad.CLIP.Luc at the permissive temperature of 32° C. No CPE appeared at the non-permissive temperature of 39° C.

TABLE 4

Complementation of E2A deletion in adenoviral vectors on 293 cells and 293 cells constitutively expressing temperature-sensitive E2A.

| Cell line | CPE at 32° C. | CPE at 39° C. |
| --- | --- | --- |
| 293pcDNA3-c4 | − | − |
| 293ts125E2A-c2 | +/− | − |
| 293ts125E2A-c16 | − | − |
| 293ts125E2A-c18 | − | − |
| 293ts125E2A-c20 | + | − |

The 293ts125E2A clones c2, c16, c18 and c20 and the 293pcDNA3-clone c4 were tested for their E2A trans-complementing activity as follows. The cell lines were either mock infected or infected with IG.Ad.CLIP.Luc at an m.o.i. of 10. Subsequently, the infected cells were cultured at either 32° C. or 39° C. and cells were screened for the appearance of a cytopathic effect (CPE) three days post infection, as determined by changes in cell morphology and detachment of the cells from the flask.

E. Serum-free Suspension Culture of PER.C6tsE2A Cell Lines.

Large-scale production of recombinant adenoviral vectors for human gene therapy requires an easy and scalable culturing method for the producer cell line, preferably a suspension culture in medium devoid of any human or animal constituents. To that end, the cell line PER.C6tsE2A c5-9 (designated c5-9) was cultured at 39° C. and 10% $CO_2$ in a 175 $cm^2$ tissue culture flask (Nunc) in DMEM, supplemented with 10% FBS and 10 mM $MgCl_2$. At sub-confluency (70-80% confluent), the cells were washed with PBS (NPBI) and the medium was replaced by 25 ml serum free suspension medium Ex-cell™ 525 (JRH) supplemented with 1×L-Glutamin (Gibco BRL), hereafter designated SFM. Two days later, cells were detached from the flask by flicking and the cells were centrifuged at 1000 rpm for 5 minutes. The cell pellet was re-suspended in 5 ml SFM and 0.5 ml cell suspension was transferred to an 80 $cm^2$ tissue culture flask (Nunc), together with 12 ml fresh SFM. After two days, cells were harvested (all cells are in suspension) and counted in a Burker cell counter. Next, the cells were seeded in a 125 ml tissue culture Erlenmeyer (Coming) at a seeding density of $3\times10^5$ cells per ml in a total volume of 20 ml SFM. Cells were further cultured at 125 RPM on an orbital shaker (GFL) at 39° C. in a 10% $CO_2$ atmosphere. Cells were counted at day 1 through 6 in a Burker cell counter. In FIG. 4, the mean growth curve from eight cultures is shown. PER.C6tsE2A c5-9 performs well in serum free suspension culture. The maximum cell density of approximately $2\times10$ cells per ml is reached within five days of culture.

F. Growth Characteristics of PER.C6 and PER.C6/E2A at 37° C. and 39° C.

PER.C6 cells or PER.C6ts125E2A (c8-4) cells were cultured in DMEM supplemented with 10% FBS and 10 mM $MgCl_2$ in a 10% $CO_2$ atmosphere at either 37° C. (PER.C6) or 39° C. (PER.C6ts125E2A c8-4). At day 0, a total of $1\times10^6$ cells were seeded per 25 $cm^2$ tissue culture flask (Nunc) and the cells were cultured at the respective temperatures. At the indicated time points, cells were counted. FIG. 5 shows that the growth of PER.C6 cells at 37° C. is comparable to the growth of PER.C6ts125E2A c8-4 at 39° C. This shows that constitutive expression of ts125E2A encoded DBP has no adverse effect on the growth of cells at the non-permissive temperature of 39° C.

G. Stability of PER.C6ts125E2A.

For several passages, the PER.C6ts125E2A cell line clone 8-4 was cultured at 39° C. and 10% $CO_2$ in a 25 $cm^2$ tissue culture flask (Nunc) in DMEM, supplemented with 10% FBS and 10 mM $MgCl_2$ in the absence of selection pressure (G418). At sub-confluency (70-80% confluent), the cells were washed with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the BioRad protein assay, according to standard procedures of the supplier (BioRad). Equal amounts of whole-cell extract were fractionated by SDS-PAGE on 10% gels. Proteins were transferred onto Immobilon-P membranes (Millipore) and incubated with the aDBP monoclonal antibody B6 (Reich et al., *Virology* 128:480, 1983). The secondary antibody was a horseradish-peroxidase-conjugated goat anti mouse antibody (Bio-Rad). The Western blotting procedure and incubations were performed according to the protocol provided by Millipore. The complexes were visualized with the ECL detection system according to the manufacturer's protocol (Amersham). FIG. 6 shows that the expression of ts125E2A encoded DBP is stable for at least 16 passages, which is equivalent to approximately 40 cell doublings. No decrease in DBP levels was observed during this culture period, indicating that the expression of ts125E2A is stable, even in the absence of G418 selection pressure.

EXAMPLE II

Plasmid-based System for the Generation of Recombinant Adenoviral Vectors Deleted in E1 and E2A A. Generation of pBr/Ad.Bam-rITR (ECACC Deposit P97082122).

In order to facilitate blunt end cloning of the inverted terminal repeat ("ITR") sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322-derived vector DNA prepared as follows: pBr322 DNA was digested with EcoRV and BamHI, de-phosphorylated by treatment with TSAP enzyme (Life Technologies) and purified on LMP agarose gel (SeaPlaque GTG). After transformation into competent *E. coli* DH5a (Life Techn.) and analysis of ampicillin resistant colonies, one clone was selected that showed a digestion pattern as expected for an insert extending from the BamHI site in Ad5 to the right ITR.

Sequence analysis of the cloning border at the right ITR revealed that the most 3' G residue of the ITR was missing, the remainder of the ITR was found to be correct. The missing G residue is complemented by the other ITR during replication.

B. Generation of pBr/Ad.Sal-rITR (ECACC Deposit P97082119).

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt AdS DNA and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

C. pBr/Ad.Cla-Bam (ECACC Deposit P97082117).

wt Adeno type 5 DNA was digested with ClaI and BamHI, and the 20.6-kb fragment was isolated from gel by electroelution. pBr322 was digested with the same enzymes and purified from agarose gel by Geneclean. Both fragments were ligated and transformed into competent DH5a. The resulting clone pBr/Ad.Cla-Bam was analyzed by restriction enzyme digestion and shown to contain an insert with adenovirus sequences from bp 919 to 21566.

D. Generation of pBr/Ad.AflII-Bam (ECACC Deposit P97082114).

Clone pBr/Ad.Cla-Bam was linearized with EcoRI (in pBr322) and partially digested with AflII. After heat inactivation of AflII for 20 minutes at 65° C., the fragment ends were filled in with Klenow enzyme. The DNA was then ligated to a blunt double stranded oligo linker containing a PacI site (5'-AATTGTCTTAATTAACCGCTTAA-3' (SEQ ID NO:3)). This linker was made by annealing the following two oligonucleotides: 5'-AATTGTCTTAATTAACCGC-3' (SEQ ID NO:4) and 5'-AATTGCGGTTAATTAAGAC-3' (SEQ ID NO:5), followed by blunting with Klenow enzyme. After precipitation of the ligated DNA to change buffer, the ligations were digested with an excess PacI enzyme to remove concatemers of the oligo. The 22016 bp partial fragment containing Ad5 sequences from bp 3534 up to 21566 and the vector sequences was isolated in LMP agarose (SeaPlaque GTG), re-ligated and transformed into competent DH5a. One clone that was found to contain the PacI site and that had retained the large adeno fragment was selected and sequenced at the 5' end to verify correct insertion of the PacI linker in the (lost) AflII site.

E. Generation of pBr/Ad.Bam-rITRpac#2 (ECACC Deposit P97082120) and pBr/Ad.Bam-rITR#8 (ECACC Deposit P97082121).

To allow insertion of a PacI site near the ITR of Ad5 in clone pBr/Ad.Bam-rITR, about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2 minutes, 5 minutes, 10 minutes and 15 minutes). The extent of nucleotide removal was followed by separate reactions on pBr322 DNA (also digested at the ClaI site), using identical buffers and conditions. Bal31 enzyme was inactivated by incubation at 75° C. for 10 minutes, and the DNA was precipitated and re-suspended in a smaller volume TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10 minutes or 15 minutes. The 10 minutes or 15 minutes treated pBr/Ad.Bam-rITR samples were then ligated to the above-described blunted PacI linkers (See pBr/Ad.AflII-Bam). Ligations were purified by precipitation, digested with excess PacI and separated from the linkers on an LMP agarose gel. After religation, DNAs were transformed into competent DH5a and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

F. Generation of pWE/Ad.AflII-rITR (ECACC Deposit P97082116).

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using 1 phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

G. Generation of pWE/Ad.AflII-EcoRI.

pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24-kb fragment containing the adenoviral sequences was isolated from agarose gel and ligated to the ClaI-digested and blunted pWE.pac vector using the Ligation Express™ kit from Clontech. After transformation of Ultra-competent XL10-Gold cells from Stratagene, clones were identified that contained the expected insert. pWE/AflII-EcoRI contains Ad5 sequences from bp 3534-27336.

H. Generation of pWE/Ad.AflII-rITRDE2A:

Deletion of the E2A coding sequences from pWE/Ad.AflII-rITR (ECACC deposit P97082116) has been accomplished as follows. The adenoviral sequences flanking the E2A coding region at the left and the right site were amplified from the plasmid pBr/Ad.Sal.rITR (ECACC deposit P97082119) in a PCR reaction with the Expand PCR system (Boehringer) according to the manufacturer's protocol. The following primers were used: Right flanking sequences (corresponding Ad5 nucleotides 24033 to 25180):

DE2A.SnaBI:
(SEQ ID NO: 6)
5'-GGC GTA CGT AGC CCT GTC GAA AG-3'

DE2A.DBP-start:
(SEQ ID NO: 7)
5'-CCA ATG CAT TCG AAG TAC TTC CTT CTC CTA TAG GC-3'.

The amplified DNA fragment was digested with SnaBI and NsiI (NsiI site is generated in the primer DE2A.DBP-start, underlined). In addition, a unique BstBI site is generated in this primer (italics).

Left flanking sequences (corresponding Ad5 nucleotides 21557 to 22442):

```
DE2A.DBP-stop:
                                        (SEQ ID NO: 8)
5'-CCA ATG CAT ACG GCG CAG ACG G-3'

DE2A.BamHI:
                                        (SEQ ID NO: 9)
5'-GAG GTG GAT CCC ATG GAC GAG-3'
```

The amplified DNA was digested with BamHI and NsiI (NsiI site is generated in the primer DE2A.DBP-stop, underlined). Subsequently, the digested DNA fragments were ligated into SnaBI/BamHI digested pBr/Ad.Sal-rITR. Sequencing confirmed the exact replacement of the DBP coding region with a unique NsiI site and BstBI site in plasmid pBr/Ad.Sal-rITRDE2A. The unique NsiI site and BstBI site can be used to introduce an expression cassette for a gene to be transduced by the recombinant vector.

The deletion of the E2A coding sequences was performed such that the splice acceptor sites of the 100K-encoding L4-gene at position 24048 in the top strand was left intact. In addition, the polyadenylation signals of the original E2A-RNA and L3-RNAs at the left-hand site of the E2A coding sequences were left intact. This ensures proper expression of the L3-genes and the gene encoding the 100K L4-protein during the adenovirus life cycle.

Next, the plasmid pWE/Ad.AflII-rITRDE2A was generated. The plasmid pBr/Ad.Sal-rITRDE2A was digested with BamHI and SpeI. The 3.9-Kb fragment in which the E2A coding region was replaced by the unique NsiI site and BstBI site was isolated. The pWE/Ad.AflII-rITR was digested with BamHI and SpeI. The 35 Kb DNA fragment, from which the BamHI/SpeI fragment containing the E2A coding sequence was removed, was isolated. The fragments were ligated and packaged using 1 phage-packaging extracts according to the manufacturer protocol (Stratagene), yielding the plasmid pWE/Ad.AflII-rITRDE2A. Note that there is no sequence overlap between the adenoviral sequences present in pWE/Ad.AflII-rITRDE2A and the E2A sequences present in the expression vectors pcDNA3tsE2A and pcDNAwtE2A or the cell lines derived from this vector.

I. Generation of the Adapter Plasmids.

Adapter plasmid pMLP.TK (European patent application no. EP 95202213) was modified as follows: SV40 polyA sequences were amplified with primer SV40-1 (introduces a BamHI site) and SV40-2 (introduces a BglII site). In addition, Ad5 sequences present in this construct (from nt. 2496 to nt. 2779; Ad5 sequences nt. 3511 to 3794) were amplified with primers Ad5-1 (introduces a BglII site) and Ad5-2.

```
SV40-1:
                                        (SEQ ID NO: 10)
5'-GGGGGATCCGAACTTGTTTATTGCAGC-3'.

SV40-2:
                                        (SEQ ID NO: 11)
5'-GGGAGATCTAGACATGATAAGATAC-3'.

Ad5-1:
                                        (SEQ ID NO: 12)
5'-GGGAGATCTGTACTGAAATGTGTGGGC-3'.

Ad5-2:
                                        (SEQ ID NO: 13)
5'-GGAGGCTGCAGTCTCCAACGGCGT-3'.
```

Both PCR fragments were digested with BglII and ligated. The ligation product was amplified with primers SV40-1 and Ad5-2 and digested with BamHI and AflII. The digested fragment was then ligated into pMLP.TK predigested with the same enzymes. The resulting construct, named pMLPI.TK, contains a deletion in adenovirus E1 sequences from nt. 459 to nt. 3510.

This plasmid was used as the starting material to make a new vector in which nucleic acid molecules comprising specific promoter and gene sequences can be easily exchanged. First, a PCR fragment was generated from pZipDMo+PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ ID NO:14) and LTR-2: 5'-GCG GAT CCT TCG AAC CAT GGT AAG CTT GGT ACC GCT AGC GTT AAC CGG GCG ACT CAG TCA ATC G-3' (SEQ ID NO:15). Pwo DNA polymerase (Boehringer Mannheim) was used according to manufacturer's protocol with the following temperature cycles: once 5 minutes at 95° C.; 3 minutes at 55° C.; and 1 minute at 72° C., and 30 cycles 1 minute at 95° C., 1 minute at 60° C., 1 minute at 72° C., followed by once for 10 minutes at 72° C. The PCR product was then digested with BamHI and ligated into pMLP10 (Levrero et al., 1991; Gene 101, 195-202) digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Sequencing confirmed correct amplification of the LTR fragment; however, most 5' bases in the PCR fragment were missing so that the PvuII site was not restored. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990; *J. Immunol.* 145, 1952-1959) using the following primers: HSA1, 5'-GCG CCA CCA TGG GCA GAG CGA TGG TGG C-3' (SEQ ID NO:16) and HSA2, 5'-GTT AGA TCT AAG CTT GTC GAC ATC GAT CTA CTA ACA GTA GAG ATG TAG AA-3' (SEQ ID NO:17). The 269 bp-amplified fragment was sub-cloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication, was then excised as a NcoI (sticky)-SalI (blunt) fragment and cloned into the 3.5 kb NcoI (sticky)/BstBI (blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd5/L420-HSA that contains convenient recognition sites for various restriction enzymes around the promoter and gene sequences. SnaBI and AvrII can be combined with HpaI, NheI, KpnI, and HindII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and polyA sequences in pAd5/L420-HSA with the CMV promoter, a multiple cloning site, an intron and a polyA signal. For this purpose, pAd/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pAd5/Clip.

The adapter plasmid pCMV.LacZ was generated as follows: The plasmid pCMV.TK (EP 95-202 213) was digested with HindIII, blunted with Klenow and dNTPs and subsequently digested with SalI. The DNA fragment containing the CMV promoter was isolated. The plasmid pMLP.nlsLacZ (EP 95-202 213) was digested with KpnI, blunted with T4 DNA polymerase and subsequently digested with SalI. The DNA fragment containing the LacZ gene and adjacent adenoviral sequences was isolated. Next, the two DNA fragments were ligated with T4 DNA ligase in the presence of ATP, giving rise to pCMV.nlsLacZ.

The adapter plasmid pAd5/CLIP.LacZ was generated as follows: The *E. coli* LacZ gene was amplified from the plasmid pMLP.nlsLacZ (EP 95-202 213) by PCR with the primers 5'-GGGGTGGCCAGGGTACCTCTAGGCTTTTGCAA (SEQ ID NO:18) and 5'-GGGGGGATCCATAAACAAGT-TCAGAATCC (SEQ ID NO:19). The PCR reaction was performed Ex Taq (Takara) according to the suppliers protocol at the following amplification program: 5 minutes 94° C., 1 cycle; 45 seconds 94° C. and 30 seconds 60° C. and 2 minutes 72° C., 5 cycles; 45 seconds 94° C. and 30 seconds 65° C. and 2 minutes 72° C., 25 cycles; 10 minutes 72° C., 1 cycle; 45 seconds 94° C. and 30 seconds 60° C. and 2 minutes 72° C., 5 cycles, 1 cycle. The PCR product was subsequently digested with KpnI and BamHI and the digested DNA fragment was ligated into KpnI/BamHI digested pcDNA3 (Invitrogen), giving rise to pcDNA3.nlsLacZ. Next, the plasmid pAd/CLIP was digested with SpeI. The large fragment containing part of the 5' part CMV promoter and the adenoviral sequences was isolated. The plasmid pcDNA3.nlsLacZ was digested with SpeI and the fragment containing the 3' part of the CMV promoter and the LacZ gene was isolated. Subsequently, the fragments were ligated, giving rise to pAd/CLIP.LacZ. The reconstitution of the CMV promoter was confirmed by restriction digestion.

The adapter plasmid pAd5/CLIP.Luc was generated as follows: The plasmid pCMV.Luc (EP 95-202 213) was digested with HindIII and BamHI. The DNA fragment containing the luciferase gene was isolated. The adapter plasmid pAd/CLIP was digested with HindIII and BamHI and the large fragment was isolated. Next, the isolated DNA fragments were ligated, giving rise to pAd5/CLIP.Luc.

EXAMPLE III

Generation of Recombinant Adenoviruses

A. E1-deleted Recombinant Adenoviruses with wt E3 Sequences.

To generate E1-deleted recombinant adenoviruses with the plasmid-based system, the following constructs are prepared:
a) An adapter construct containing the expression cassette with the gene of interest linearized with a restriction enzyme that cuts at the 3' side of the overlapping adenoviral genome fragment, preferably not containing any pBr322 vector sequences, and
b) A complementing adenoviral genome construct pWE/Ad.AflII-rITR digested with PacI. These two DNA molecules are further purified by phenol/chloroform extraction and ethanol precipitation. Co-transfection of these plasmids into an adenovirus packaging cell line, preferably a cell line according to the invention, generates recombinant replication deficient adenoviruses by a one-step homologous recombination between the adapter and the complementing construct.

A general protocol as outlined hereinafter and meant as a non-limiting example of the present invention has been performed to produce several recombinant adenoviruses using various adapter plasmids and the Ad.AflII-rITR fragment. Adenovirus packaging cells (PER.C6) were seeded in ~25 cm$^2$ flasks and the next day, when they were at ~80% confluency, transfected with a mixture of DNA and lipofectamine agent (Life Techn.) as described by the manufacturer. Routinely, 40 μl lipofectamine, 4 μg adapter plasmid and 4 μg of the complementing adenovirus genome fragment AflII-rITR (or 2 μg of all three plasmids for the double homologous recombination) are used. Under these conditions, transient transfection efficiencies of ~50% (48 hours post transfection) are obtained as determined with control transfections using a pAd/CMV-LacZ adapter. Two days later, cells are passaged to ~80 cm$^2$ flasks and further cultured. Approximately five (for the single homologous recombination) to eleven days (for the double homologous recombination) later a cytopathic effect (CPE) is seen, indicating that functional adenovirus has formed. Cells and medium are harvested upon full CPE and recombinant virus is released by freeze-thawing. An extra amplification step in a 80 cm$^2$ flask is routinely performed to increase the yield since at the initial stage the titers are found to be variable despite the occurrence of full CPE. After amplification, viruses are harvested and plaque purified on PER.C6 cells. Individual plaques are tested for viruses with active trans-genes.

Several different recombinant adenoviruses, comprising the luciferase gene (IG.Ad.CLIP.Luc), the bacterial LacZ gene (IG.Ad.CLIP.LacZ and IG.Ad.CMV.LacZ) or an empty CLIP cassette (IG.Ad.CLIP) have been produced using this protocol. In all cases, functional adenovirus was formed and all isolated plaques contained viruses with the expected expression cassettes.

B. Generation of Recombinant Adenoviruses Deleted for E1 and E2A.

Besides replacements in the E1 region, it is possible to delete or replace the E2A region in the adenovirus. This creates the opportunity to use a larger insert or to insert more than one gene without exceeding the maximum packagable size (approximately 105% of wt genome length).

Recombinant viruses that are both E1 and E2A deleted are generated by a homologous recombination procedure as described above for E1-replacement vectors using a plasmid-based system consisting of:
a) An adapter plasmid for E1 replacement according to the invention, with or without insertion of a first gene of interest.
b) The pWE/Ad.AflII-rITRDE2A fragment, with or without insertion of a second gene of interest.

Generation and propagation of such viruses, e.g., IG.Ad.CMV.LacZDE2A, IG.Ad.CLIP.LacZDE2A, IG.Ad.CLIPDE2A or IG.Ad.CLIP.LucDE2A, requires a complementing cell line for complementation of both E1 and E2A proteins in trans, as previously described herein.

In addition to replacements in the E1 and E2A region, it is also possible to delete or replace (part of) the E3 region in the E1-deleted adenoviral vector, because E3 functions are not necessary for the replication, packaging and infection of the (recombinant) virus. This creates the opportunity to use larger inserts or to insert more than one gene without exceeding the maximum packagable size (approximately 105% of wt genome length). This can be done, e.g., by deleting part of the E3 region in the pBr/Ad.Bam-rITR clone by digestion with XbaI and re-ligation. This removes Ad5 wt sequences 28592-30470 including all known E3 coding regions. Another example is the precise replacement of the coding region of gp19K in the E3 region with a polylinker allowing insertion of new sequences. This 1) leaves all other coding regions intact and 2) obviates the need for a heterologous promoter since the transgene is driven by the E3 promoter and pA sequences, leaving more space for coding sequences.

To this end, the 2.7-kb EcoRI fragment from wt Ad5 containing the 5' part of the E3 region was cloned into the EcoRI site of pbluescript (KS⁻) (Stratagene). Next, the HindIII site in the polylinker was removed by digestion with EcoRV and HincII and subsequent re-ligation. The resulting clone pBS.Eco-Eco/ad5DHIII was used to delete the gp19K-coding region. Primers 1 (5'-GGG TAT TAG GCC AAA GGC GCA-3' (SEQ ID NO:20)) and 2 (5'-GAT CCC ATG GAA GCT TGG GTG GCG ACC CCA GCG-3' (SEQ ID NO:21)) were used to amplify a sequence from pBS.Eco-Eco/ad5DHIII corresponding to sequences 28511 to 28734 in wt Ad5 DNA. Primers 3 (5'-GAT CCC ATG GGG ATC CTT TAC TAA GTT ACA AAG CTA-3' (SEQ ID NO:22)) and 4 (5'-GTC GCT GTA GTT GGA CTG G-3' (SEQ ID NO:23)) were used on the same DNA to amplify Ad5 sequences from 29217 to 29476. The two resulting PCR fragments were ligated together by virtue of the new introduced NcoI site and subsequently digested with XbaI and MunI. This fragment was then ligated into the pBS.Eco-Eco/ad5DHIII vector that was digested with XbaI (partially) and MunI generating pBS.Eco-Eco/ad5DHIII.Dgp19K. To allow insertion of foreign genes into the HindIII and BamHI site, an XbaI deletion was made in pBS.Eco-Eco/ad5DHIII.Dgp19K to remove the BamHI site in the Bluescript polylinker. The resulting plasmid pBS.Eco-Eco/ad5DHIII.Dgp19KDXbaI, contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is re-cloned into pBS.Eco-Eco/ad5DHIII.Dgp19K using HindIII and, for example, MunI. Using this procedure, we have generated plasmids expressing HSV-TK, hIL-1a, rat IL-3, luciferase or LacZ. The unique SrfI and NotI sites in the pBS.Eco-Eco/ad5DHIII.Dgp19K plasmid (with or without inserted gene of interest) are used to transfer the region comprising the gene of interest into the corresponding region of pBr/Ad.Bam-rITR, yielding construct pBr/Ad.Bam-rITRDgp19K (with or without inserted gene of interest). This construct is used as described supra to produce recombinant adenoviruses. In the viral context, expression of inserted genes is driven by the adenovirus E3 promoter.

Recombinant viruses that are both E1 and E3 deleted are generated by a double homologous recombination procedure for E1-replacement vectors using a plasmid-based system consisting of:
a) an adapter plasmid for E1 replacement according to the invention, with or without insertion of a first gene of interest,
b) the pWE/Ad.AflII-EcoRI fragment, and
c) the pBr/Ad.Bam-rITRDgp19K plasmid with or without insertion of a second gene of interest.

In addition to manipulations in the E3 region, changes of (parts of) the E4 region can be accomplished easily in pBr/Ad.Bam-rITR. Moreover, combinations of manipulations in the E3 and/or E2A and/or E4 region can be made. Generation and propagation of such vectors, however, demands packaging cell lines that complement for E1 and/or E2A and/or E4 in trans.

EXAMPLE IV

E2A Revertant-free Manufacturing of E1/E2A-deleted Vectors on PER.C6/E2A Cells

The cell lines and E1/E2A-deleted vectors described hereinbefore are developed such that overlap between sequences in the recombinant adenoviral genome and E2A sequences in the complementing cell lines is avoided. This eliminates reversion of the E2A-deleted phenotype in the E1/E2A-deleted recombinant adenoviral vectors due to homologous recombination. The occurrence of reversion of the E2A-deleted phenotype was studied in a PCR assay.

PER.C6tsE2A clone 3-9 cells were cultured in DMEM supplemented with 10% FBS and 10 mM $MgCl_2$ in a 10% $CO_2$ atmosphere at 39° C. in a 25 $cm^2$ tissue culture flask. At 50% confluency, cells were infected with the recombinant adenoviral vector IG.Ad.CMV.LacZDE2A and the cells were put at 32° C. Four days post infection CPE appeared and the cells were harvested by flicking the flask. Cells were pelleted by centrifugation and the cell pellet was re-suspended in 1 ml/10 mM phosphate buffer (18 ml 0.2M $Na_2HPO_4$ (Baker) and 7 ml 0.2M $NaH_2PO_4$ (Merck) in 500 ml $H_2O$ pH=7.2). Next, 200 µl 5% sodium deoxycholate (Sigma) was added. The mixture was incubated for 30 minutes at 37° C. and 50 µl 1 M $MgCl_2$ and 10 µl DNase (1 MU/ml; ICN) was added. The mixture was incubated for another half hour at 37° C. and than cleared by centrifugation. The supernatant was put into a new tube and 100 µl 10% SDS (Baker) and 5 µl Proteinase K (20 mg/ml; Boehringer) were added. The mixture was incubated for 30 minutes at 37° C. and subsequently for 15 minutes at 65° C. Next, 1 ml phenol (Sigma) was added and the mixture was tumbled for one hour and centrifuged. One ml of supernatant was put into a fresh tube and 1 ml chloroform (Baker) was added. The mixture was tumbled for another 30 minutes and centrifuged. The supernatant was put into a fresh tube and mixed with 1 ml 2-Propanol (Baker) and the DNA was pelleted by centrifugation. The DNA was washed in 70% Ethanol (Baker) and re-suspended in 200 µl TE and 1 µl RNase (10 mg/ml; Boehringer). The DNA concentration was determined at a spectrophotometer.

The recombinant adenoviral vector DNA was screened for reversion of the E2A-deleted phenotype by PCR. Two PCR reactions were performed (FIG. 7). The first was a nested PCR reaction for the detection of E2A sequences in the DNA sample. Two primer sets were designed. Set A contains the primers 551: 5'-CCGGCAAGTCTTGCGGCATG (SEQ ID NO:24) and 556: 5'-TAGCAGGTCGGGCGCCGATAT (SEQ ID NO:25) and the nested primers 553: 5'-GGCTCAG-GTGGCTTTTAAGCAG (SEQ ID NO:26) and 554: 5'-GAGTTGCGATACACAGGGTTGC (SEQ ID NO:27). The PCR reaction was performed using the eLONGase enzyme mix (Gibco) according to the manufacturer's protocol. DNA from $1 \times 10^9$ viral particles (+), which is equivalent to ~40 ng, or water (−) was added as template. The PCR reactions were either not spiked, or spiked with 1, 10 and 40 molecules pBR/Ad.Sal-rITR, respectively, as indicated in FIG. 7. The following amplification program for the PCR reaction with primers 551 and 556 was used: 30 seconds at 94° C., 1 cycle; 30 seconds 94° C. and 30 seconds at 66° C. and 90 seconds at 68° C., 35 cycles; 10 minutes 68° C., 1 cycle. One µl of this reaction was put into a nested PCR with primers 553 and 554 at the following amplification program: 30 seconds at 94° C., 1 cycle; 30 seconds 94° C. and 30 seconds at 66° C. and 90 seconds at 68° C., 35 cycles; 10 minutes 68° C., 1 cycle. This reaction yields a DNA fragment of 260 bp.

In the second PCR reaction, a set of primers (Set B) was used that flank the E2A gene in the adenoviral genome on the left- and the right-hand site. This PCR reaction amplifies a DNA fragment spanning the site from which the E2A gene was deleted (FIG. 6). Primer set B comprises primer 731 5'-AGTGCGCAGATTAGGAGCGC (SEQ ID NO:28) and primer 734 5'-TCTGCCTATAGGAGAAGGAA (SEQ ID NO:29). The PCR reaction was performed using the eLONGase enzyme mix (Gibco) according to the manufacturer protocol. DNA from $1\times10^9$ viral particles (+), which is equivalent to ~40 ng, or water (−) was added as template. The PCR reactions were either not spiked, or spiked with 1, 10 and 40 molecules pBR/Ad.Sal-rITR, respectively, as indicated in FIG. 7. The following amplification program was used: 30 seconds at 94° C., 1 cycle; 30 seconds 94° C. and 30 seconds at 50° C. and 90 seconds at 68° C., 35 cycles; 10 minutes 68° C., 1 cycle. This PCR reaction yields a DNA fragment of 169 bp.

As shown in FIG. 7, left panel (set A), E2A sequences were amplified from the DNA samples (+) and control samples (−) spiked with both 1, 10 and 40 molecules, as evidenced by the amplification of a 260 bp DNA fragment. In contrast, no E2A sequences were amplified from the non-spiked samples. This shows that reversion of the E2A-deleted does not occur. The PCR reactions with primers 731/734 yielded the expected DNA fragment of 169 bp in the samples containing the recombinant adenoviral vector DNA (+). From the negative control samples containing the water instead of DNA (−), no DNA fragment of 169 bp was amplified. These data show that elimination of overlap between adenoviral sequences in the vector and cell line prevents reversion of the E2A-deleted phenotype.

EXAMPLE V

Transduction Capacity of and Residual Expression of Adenoviral Genes from E1-deleted and E1/E2A-deleted Recombinant Adenoviral Vectors The transduction capacity of E1/E2A-deleted vectors was compared to E1-deleted vectors. HeLa cells were seeded at $5\times10^5$ cells/well in 6-well plates (Greiner) in DMEM supplemented with 10% FBS in a 10% $CO_2$ atmosphere at 37° C. The next day, cells were infected with a m.o.i. of either 0, 10, 100 or 1000 viral particles IG.Ad/CMV.LacZ or IG.Ad/CMV.LacZDE2A per cell. Forty-eight hours post infection, cells were washed with PBS (NPBI) and fixed for 8 minutes in 0.25% glutaraldehyde (Sigma) in PBS (NPBI). Subsequently, the cells were washed twice with PBS and stained for eight hours with X-gal solution (1 mg/ml X-gal in DMSO (Gibco), 2 mM $MgCl_2$ (Merck), 5 mM $K_4[Fe(CN)_6].3H_2O$ (Merck), 5 mM $K_3[Fe(CN)_6]$ (Merck) in PBS. The reaction was stopped by removal of the X-gal solution and washing of the cells with PBS. FIG. 8 shows that IG.Ad/CMV.LacZDE2A transduced HeLa cells at least as good as did IG.Ad/CMV.LacZ at all m.o.i.s. Comparable results were obtained after infection of IG.Ad.CLIP.LacZ and IG.Ad.CLIP.LacZDE2A and after infection of A549 cells with the respective recombinant adenoviral vectors. These data show that the viral particle to transduction unit ratio (vp/tu) of E1/E2A-deleted vectors (e.g., IG.Ad/CMV.LacZDE2A) is at least as good as the vp/tu of E1-deleted vectors (e.g., IG.Ad/CMV.LacZ).

Next, the vp/tu ratio of E1- and E1/E2A-deleted vectors was determined in a more sensitive assay, i.e., a luciferase assay. HeLa and A549 cells were seeded at 5×105 cells/well in 6-well plates (Greiner) in DMEM supplemented with 10% FBS in a 10% $CO_2$ atmosphere at 37° C. The next day, cells were infected with a m.o.i. of either 0, 10, 100, 1,000 or 10,000 vp/cell IG.Ad/CLIP.Luc or IG.Ad/CLIP.LucDE2A per cell. Two days post infection, cells were lysed and the luciferase activity was determined with the Luciferase Assay System according to the protocol of the supplier (Promega). FIG. 9 shows that both the IG.Ad/CLIP.LucDE2A infected HeLa and A549 cells produce more luciferase enzyme than the IG.Ad/CLIP.Luc infected HeLa and A549 and HeLa cells, at all m.o.i.s tested. These data confirm that E1/E2A-deleted recombinant adenoviral vectors produced on PER.C6ts125E2A cells have a vp/tu ratio that is at least as good as the vp/tu ratio of E1-deleted vectors. The above is in contrast to what has recently been reported by others (O'Neal et al., 1998; Lusky et al., 1998), who found that the vp/tu ratio of E1/E2A-deleted recombinant adenoviral vectors is impaired significantly. However, these vectors were produced on two independent 293-based E2A-complementing cell lines harboring inducible E2A genes. This suggests that the use of temperature-sensitive E2A genes, such as ts125E2A, yields superior E2A-complementing cell lines as compared to the commonly used inducible E2A genes.

In order to test whether E1/E2A-deleted vectors residually express adenoviral proteins, the following experiment has been performed. A549 cells were seeded on 6-well plates (Greiner) at a density of $5\times10^5$ cells/well in DMEM supplemented with 10% FBS in a 10% $CO_2$ atmosphere at 37° C. The next day, cells were infected with a m.o.i. of either 0, 100, 1,000 or 10,000 vp/cell IG.Ad/CLIP or IG.Ad.CLIPDE2A. After 12 hours, the infection medium was replaced by fresh DMEM supplemented with 10% FBS. Seventy-two hours post infection, the cells were washed with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the BioRad protein assay, according to standard procedures of the supplier (BioRad). Equal amounts of whole-cell extract were fractionated by SDS-PAGE on 10% gels in triplicate. Proteins were transferred onto Immobilon-P membranes (Millipore) and incubated with the aDBP monoclonal antibody B6, the polyclonal a-Penton base antibody Ad2-Pb571 (kind gift of Dr. P. Boulanger, Montpellier, France) and the polyclonal a-knob domain antibody of fiber E641/3 (kind gift of R. Gerard, Leuven, Belgium). The secondary antibodies were a horseradish-peroxidase-conjugated goat anti mouse and a horseradish-peroxidase-conjugated goat anti rabbit (BioRad). The Western blotting procedure and incubations were performed according to the protocol provided by Millipore. The complexes were visualized with the ECL detection system according to the manufacturer's protocol (Amersham). FIG. 10 shows that cells infected with IG.Ad.CLIP express both E2A encoded DBP, Penton base and Fiber proteins. The proteins co-migrated with the respective proteins in the positive control (lane P, extract from PER.C6 cells infected with IG.Ad.CLIP harvested at starting CPE). The residual expression of these proteins in A549 cells was m.o.i. dependent. In contrast, no DBP, penton-base or fiber was detected in the non-infected A549 cells or cells infected with IG.Ad.CLIPDE2A. These data show that deletion of the E2A gene did not only eliminate residual DBP expression, but also the residual expression of the late adenoviral proteins, penton-base and fiber.

In conclusion, the foregoing shows that E1/E2A-deleted vectors produced on PER.C6/tsE2A-complementing cell lines have a favorable phenotype. First, these vectors have an ideal vp/tu ratio, which is at least as good as that of E1-deleted vectors. Second, the E1/E2A-deleted vectors do not residually express detectable amounts of E2A encoded DBP or late gene encoded penton-base or fiber. This favorable phenotype improves the prospects for the use of recombinant adenoviral vectors in gene therapy.

What is claimed is:

1. A packaging system for production of recombinant adenovirus without the concomitant generation of adenovirus having a functional E1 region, the packaging system comprising:
   a packaging cell containing, integrated into its genome, a nucleic acid encoding adenoviral E1A and E1B gene products, wherein said nucleic acid lacks sequences that encode adenoviral pIX protein; and
   a recombinant adenovirus vector with a deletion in the E1 region, said recombinant adenovirus vector comprising a nucleic acid molecule that encodes adenoviral pIX protein, said recombinant adenovirus vector lacking overlapping sequences with the nucleic acid encoding E1A and E1B gene products that lead to homologous recombination in said cell resulting in the formation of adenovirus having a functional E1 region.

2. The packaging system of claim 1, wherein said packaging cell is of human origin.

3. A packaging system for producing recombinant adenovirus without the concomitant generation of adenovirus having a functional E1 region, the packaging system comprising:
   a packaging cell, wherein said packaging cell is of primary cell origin, containing, integrated into its genome, a polynucleotide encoding adenoviral E1A and E1B gene products, but lacking sequences encoding adenoviral pIX protein; and
   a recombinant adenovirus vector with a deletion in the E1 region, the recombinant adenovirus vector comprising a polynucleotide encoding adenoviral pIX protein, said recombinant adenovirus vector lacking overlapping sequences with the polynucleotide encoding adenoviral E1A and E1B gene products that lead to homologous recombination in the packing cell resulting in the formation of adenovirus having a functional E1 region.

4. A packaging system for producing recombinant adenovirus without the concomitant generation of adenovirus having a functional E1 region, the packaging system comprising:
 a packaging cell, wherein said packaging cell is of human embryonic retinoblast origin, containing, integrated into its genome, a polynucleotide encoding adenoviral E1A and E1B gene products, but lacking sequences encoding adenoviral pIX protein; and
 a recombinant adenovirus vector with a deletion in the E1 region, the recombinant adenovirus vector comprising a polynucleotide encoding adenoviral pIX protein, said recombinant adenovirus vector lacking overlapping sequences with the polynucleotide encoding adenoviral E1A and E1B gene products that lead to homologous recombination in the packing cell resulting in the formation of adenovirus having a functional E1 region.

5. A packaging system for producing recombinant adenovirus without the concomitant generation of adenovirus having a functional E1 region, the packaging system comprising:
 a packaging cell containing, integrated into its genome, a polynucleotide encoding adenoviral E1A and E1B gene products, wherein said polynucleotide encoding adenoviral E1A and E1B gene products is under control of a heterologous promoter and lacks sequences encoding adenoviral pIX protein; and
 a recombinant adenovirus vector with a deletion in the E1 region, the recombinant adenovirus vector comprising a polynucleotide encoding adenoviral pIX protein, said recombinant adenovirus vector lacking overlapping sequences with the polynucleotide encoding adenoviral E1A and E1B gene products that lead to homologous recombination in the packing cell resulting in the formation of adenovirus having a functional E1 region.

6. The packaging system of claim 5, wherein said heterologous promoter is a human PGK promoter.

7. A packaging system for production of recombinant adenovirus without the concomitant generation of adenovirus having a functional E1 region, the packaging system comprising:
 a packaging cell containing integrated into its genome a nucleic acid encoding adenoviral E1A and E1B gene products, wherein said nucleic acid lacks sequences that encode adenoviral pIX protein; and
 a recombinant adenovirus vector with a deletion in the E1 region, the recombinant adenovirus vector comprising a nucleic acid molecule that encodes adenoviral pIX protein, the recombinant adenovirus vector lacking overlapping sequences with the nucleic acid encoding E1A and E1B gene products that lead to homologous recombination in said cell resulting in the formation of adenovirus having a functional E1 region, wherein said nucleic acid encoding adenoviral E1A and E1B gene products consists of nucleotides 459-3510 of the E1 region of human adenovirus 5.

8. The packaging system according to claim 7, wherein said packaging cell is a PER.C6 cell, as deposited under no. 96022940 at the European Collection of Animal Cell Cultures.

9. The packaging system according to claim 1, wherein said packaging cell further comprises a nucleic acid encoding an adenoviral E2A gene product.

10. The packaging system according to claim 9, wherein said adenoviral E2A gene product comprises the temperature-sensitive E2A ts125 mutation.

11. The packaging system according to claim 1, wherein said recombinant adenovirus vector with a deletion in the E1 gene has a deletion of nucleotides 459-3510 of the E1 gene.

12. A packaging system for producing recombinant adenovirus without the concomitant generation of adenovirus having a functional E1 region, the packaging system comprising:
 a packaging cell containing, integrated into its genome, a polynucleotide encoding adenoviral E1A and E1B gene products, but lacking sequences encoding adenoviral pIX protein; and
 a recombinant adenovirus vector with a deletion in the E1 region, wherein said recombinant adenovirus vector with a deletion in the E1 gene comprises a polynucleotide encoding adenoviral pIX protein and a nucleic acid molecule of interest, said recombinant adenovirus vector lacking overlapping sequences with the polynucleotide encoding adenoviral E1A and E1B gene products that lead to homologous recombination in the packing cell resulting in the formation of adenovirus having a functional E1 region.

13. A packaging system for production of recombinant adenovirus without the concomitant generation of adenovirus having a functional E1 region, the packaging system comprising:
 a packaging cell containing a nucleic acid encoding adenoviral E1A and E1B gene products, wherein the nucleic acid lacks sequences that encode adenoviral pIX protein, wherein the packaging cell is obtained from a cell as deposited under No. 96022940 at the European Collection of Animal Cell Cultures; and
 a recombinant adenovirus vector with a deletion in the E1 region, the recombinant adenovirus vector lacking overlapping sequences with the nucleic acid encoding E1A and E1B gene products that lead to homologous recombination thereof in the packaging cell resulting in the formation of adenovirus having a functional E1 region.

14. The packaging system according to claim 13, wherein the packaging cell further comprises an E1A-independent transcriptional initiation region operatively linked to an adenoviral E2A region.

15. The packaging system according to claim 13, wherein the packaging cell further comprises a packaging construct comprising a mutation in an adenoviral E2A region such that at least one E2A gene product is temperature sensitive.

16. The packaging system according to claim 13, wherein the recombinant adenovirus vector comprises a portion from a human adenovirus 5 genome from which nucleotides 459-3510 have been deleted.

17. The packaging system according to claim 13, wherein the packaging cell further comprises a packaging construct comprising a transcriptional initiation region operatively linked to an adenoviral E2A region having a temperature-sensitive ts125 mutation.

18. The packaging system according to claim 13, wherein the recombinant adenovirus vector with a deletion in the E1 gene comprises a nucleic acid of interest.

* * * * *

UNITED STATES PATENT AND TRADEMARK OFFICE
CERTIFICATE OF CORRECTION

PATENT NO. : 8,236,293 B2
APPLICATION NO. : 11/134674
DATED : August 7, 2012
INVENTOR(S) : Frits J. Fallaux et al.

It is certified that error appears in the above-identified patent and that said Letters Patent is hereby corrected as shown below:

On the title page:
In ITEM (75) Inventors:  delete "Govert Schoutten, Leiden (NL)"

In ITEM (56) References Cited:
OTHER PUBLICATIONS
Page 5, 1st column, insert before the 17th entry (line 50), insert --FISHER et al., "Recombinant Adenovirus Deleted of All Viral Genes for Gene Therapy of Cystic Fibrosis," Virology, 217:11-22, 1996.
FLOMENBERG et al., "Molecular Epidemiology of Adenovirus Type 35 Infections in Immunocompromised Hosts," The Journal of Infectious Diseases vol. 155, No. 6, June 1987.
FLOMENBERG et al., Sequence and Genetic Organization of Adenovirus Type 35 Early Region 3; Journal of Virology, November 1988, pp. 4431-4437, vol. 62, No. 11.
From Japanese Prosecution: MAAT et al., The Nucleotide sequence of adenovirus type 5 early region E1: the region between map positions 8.0 (hindIII site) and 11.8 (SmaI site), Gene, 1980, pp. 27-38, vol. 10.
GALL et al., "Adenovirus Type 5 and 7 Capsid Chimera: Fiber Replacement Alters Receptor Tropism without Affecting Primary Immune Neutralization Epitopes," Journal of Virology, Apr. 1996, p. 2116-2123.

Signed and Sealed this
Nineteenth Day of March, 2013

Teresa Stanek Rea
*Acting Director of the United States Patent and Trademark Office*

CERTIFICATE OF CORRECTION (continued)
U.S. Pat. No. 8,236,293 B2

In ITEM (56) References Cited:
OTHER PUBLICATIONS
Page 5, 1st column, insert before the
17th entry (line 50),      GALL et al., "Construction and Characterization of Hexon-Chimeric Adenoviruses: Specification of adenovirus serotype," 72(12) Journal of Virology, 10260-64 (1998).
GALLIMORE et al., "Transformation of Human Embryo Retinoblasts with Simian Virus 40, Adenovirus and RAS Oncogenes," Anticancer Research, 1986, pp. 499-508, vol. 6.
GAO et al., "Biology of Adenovirus Vectors with E1 and E4 Deletions for Liver-Directed Gene Therapy," Journal of Virology, 70(12):8934-8943, December 1996. Garnier et al., Scale-up of the adenovirus expression system for the production of recombinant protein in human 293S cells, Cytotechnology, 1994, pp. 145-55, vol. 15. GenBank Accession No. X02996.1, 1993, "Adenovirus type 5 left 32% of the genome."--

| | | |
|---|---|---|
| COLUMN 2, | LINE 6 | change "☐b2-microglobulin" to --β2-microglobulin-- |
| COLUMN 7, | LINES 3, 4 | change "CG<u>GGATCC</u>G CCA CCA TGG CCA GTC GGG AAG AGG AG" to --CGG GAT CC*G CCA CC*A TGG CCA GTC GGG AAG AGG AG-- |
| COLUMN 7, | LINES 7, 8 | change "CG<u>GAATTC</u>T TAA AAA TCA AAG GGG TTC TGC CGC" to --CGG AAT TCT TAA AAA TCA AAG GGG TTC TGC CGC-- |
| COLUMN 7, | LINE 51 | change "LipoFectAMINE PLUS™" to --LIPOFECTAMINE PLUS™-- |
| COLUMN 11, | LINE 59 | change "(Coming)" to --(Corning)-- |
| CLAIM 5, COLUMN 33, | LINE 37 | change "packing cell" to --packaging cell-- |
| CLAIM 12, COLUMN 34, | LINE 24 | change "the packing" to --the packaging-- |
| CLAIM 17, COLUMN 34, | LINE 59 | change "sensitive is 125" to --sensitive ts125-- |

SEQUENCE LISTING

```
<160> NUMBER OF SEQ ID NOS: 29

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: primer
      DBPpcr1

<400> SEQUENCE: 1
cgggatccgc caccatggcc agtcgggaag aggag                              35

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: primer
      DBPpcr2

<400> SEQUENCE: 2
cggaattctt aaaaatcaaa ggggttctgc cgc                                33

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: oligo
      linker containing PacI site

<400> SEQUENCE: 3
aattgtctta attaaccgct taa                                           23

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      oligonucleotide used to form oligo
      linker described by SEQ. ID. NO.: 3

<400> SEQUENCE: 4
aattgtctta attaaccgc                                                19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      oligonucleotide used to form oligo
      linker described by SEQ. ID. NO.: 3

<400> SEQUENCE: 5
aattgcggtt aattaagac                                                19

<210> SEQ ID NO 6
```

-continued

```
<211> LENGTH: 23
<212> TYPE: DNA
<213> ORGANISM: Artificial Sequence
<220> FEATURE:
<223> OTHER INFORMATION: Description of Artificial Sequence: primer
      DE2A.SnaBI

<400> SEQUENCE: 6
ggcgtacgta gccctgtcga aag                                           23

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: primer
      DE2A.DBP start

<400> SEQUENCE: 7
ccaatgcatt cgaagtactt ccttctccta taggc                              35

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer
      DE2A.DBP stop

<400> SEQUENCE: 8
ccaatgcata cggcgcagac gg                                            22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer
      DE2A.BamHI

<400> SEQUENCE: 9
gaggtggatc ccatggacga g                                             21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: primer
      SV40 1

<400> SEQUENCE: 10
gggggatccg aacttgttta ttgcagc                                       27

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: primer
      SV40 2

<400> SEQUENCE: 11
gggagatcta gacatgataa gatac                                         25

<210> SEQ ID NO 12
<211> LENGTH: 27
<212> TYPE: DNA
```

```
<213> ORGANISM: Artificial Sequence
<220> FEATURE:
<223> OTHER INFORMATION: Description of Artificial Sequence: primer
      Ad5 1

<400> SEQUENCE: 12
gggagatctg tactgaaatg tgtgggc                                          27

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: primer
      Ad5 2

<400> SEQUENCE: 13
ggaggctgca gtctccaacg gcgt                                             24

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: primer
      LTR 1

<400> SEQUENCE: 14
ctgtacgtac cagtgcactg gcctaggcat ggaaaaatac ataactg                    47

<210> SEQ ID NO 15
<211> LENGTH: 63
<212> TYPE: DNA
<213> ORGANISM: Artificial Sequence
<220> FEATURE:
<223> OTHER INFORMATION: Description of Artificial Sequence: primer
      LTR 2

<400> SEQUENCE: 15
gcggatcctt cgaaccatgg taagcttggt accgctagcg ttaaccgggc gactcagtca atc  63

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: primer
      HSA1

<400> SEQUENCE: 16
gcgccaccat gggcagagcg atggtgg                                          27

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: primer
      HSA2

<400> SEQUENCE: 17
gttagatcta agcttgtcga catcgatcta ctaacagtag agatgtagaa                 50

<210> SEQ ID NO 18
<211> LENGTH: 32
<212> TYPE: DNA
<213> ORGANISM: Artificial Sequence
<220> FEATURE:
```

<223> OTHER INFORMATION: Description of Artificial Sequence: primer
      used for amplification of E. coli LacZ

<400> SEQUENCE: 18
ggggtggcca gggtacctct aggcttttgc aa                                32

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: primer
      used for amplification of E. coli LacZ

<400> SEQUENCE: 19 gggggatcc ataaacaagt tcagaatcc                                     29

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: primer 1

<400> SEQUENCE: 20
gggtattagg ccaaaggcgc                                              20

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: primer 2

<400> SEQUENCE: 21
gatcccatgg aagcttgggt ggcgacccca gcg                               33

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: primer 3

<400> SEQUENCE: 22
gatcccatgg ggatcctta ctaagttaca aagcta                             36

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: primer 4

<400> SEQUENCE: 23
gtcgctgtag ttggactgg                                               19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: primer 551

<400> SEQUENCE: 24
ccggcaagtc ttgcggcatg                                              20

```
<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: primer 556

<400> SEQUENCE: 25
tagcaggtcg ggcgccgata t                                              21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: primer 553

<400> SEQUENCE: 26
ggctcaggtg gcttttaagc ag                                             22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: primer 554

<400> SEQUENCE: 27
gagttgcgat acacagggtt gc                                             22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: primer 731

<400> SEQUENCE: 28
agtgcgcaga ttaggagcgc                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: primer 734

<400> SEQUENCE: 29
tctgcctata ggagaaggaa                                                20
```